(12) United States Patent
Sears et al.

(10) Patent No.: US 10,076,619 B2
(45) Date of Patent: Sep. 18, 2018

(54) VENT ARRANGEMENT FOR RESPIRATORY MASK

(71) Applicant: ResMed Limited, Bella Vista (AU)

(72) Inventors: David Brent Sears, Woodland Hills, CA (US); Steven Paul Farrugia, Lugarno (AU); Aleksandr S. Nagorny, Canoga Park, CA (US); Richard G. Krum, Camarillo, CA (US); Joseph M. Sampietro, Tarzana, CA (US)

(73) Assignee: ResMed Limited (AU)

( * ) Notice: Subject to any disclaimer, the term of this patent is extended or adjusted under 35 U.S.C. 154(b) by 710 days.

(21) Appl. No.: 13/967,609

(22) Filed: Aug. 15, 2013

(65) Prior Publication Data

US 2014/0069428 A1    Mar. 13, 2014

Related U.S. Application Data

(60) Provisional application No. 61/699,520, filed on Sep. 11, 2012.

(51) Int. Cl.
*A61M 16/00* (2006.01)
*A61M 16/06* (2006.01)
(Continued)

(52) U.S. Cl.
CPC .......... *A61M 16/009* (2013.01); *A61M 16/00* (2013.01); *A61M 16/0057* (2013.01);
(Continued)

(58) Field of Classification Search
CPC .............. A61M 16/009; A61M 16/205; A61M 16/0057; A61M 16/00; A61M 16/20;
(Continued)

(56) References Cited

U.S. PATENT DOCUMENTS 1,407,216 A    2/1922   Potter
3,101,736 A    8/1963   Egger
(Continued)

FOREIGN PATENT DOCUMENTS

CN    1886167 A    12/2006
EP    0266963 A2   5/1988
(Continued)

OTHER PUBLICATIONS

Extended European Search Report for Application No. 13183779 dated Mar. 31, 2014.
(Continued)

*Primary Examiner* — Jackie Tan-Uyen T Ho
*Assistant Examiner* — Joseph D Boecker
(74) *Attorney, Agent, or Firm* — Lerner, David, Littenberg, Krumholz & Mentlik, LLP

(57) ABSTRACT

A control system provides automated control of gas washout of a patient interface, such as a mask or nasal prongs. A gas washout vent assembly of the system may include a variable exhaust area, such as one defined by gears, radial exhaust revolvers and/or flow diverters for a conduit having a variable gas passage channel. The vent assembly may be attached substantially near or included with the patient interface. An actuator of the assembly, such as a solenoid, motor or voice coil, manipulates the vent assembly. The actuator may be configured for control by a processor to change the exhaust area of the vent assembly based on various methodologies including, for example, sleep detection, disordered breathing event detection and/or leak detection.

12 Claims, 16 Drawing Sheets

(51) Int. Cl.
   *A61M 16/20* (2006.01)
   *F16K 5/04* (2006.01)
   *F16K 11/072* (2006.01)
   *F16K 11/087* (2006.01)
   *A61M 16/08* (2006.01)
   *A61M 16/16* (2006.01)
   *A61M 16/10* (2006.01)

(52) U.S. Cl.
   CPC ........ *A61M 16/0069* (2014.02); *A61M 16/20* (2013.01); *A61M 16/205* (2014.02); *F16K 5/0407* (2013.01); *F16K 11/072* (2013.01); *F16K 11/0873* (2013.01); *A61M 16/0066* (2013.01); *A61M 16/06* (2013.01); *A61M 16/0672* (2014.02); *A61M 16/0816* (2013.01); *A61M 16/0825* (2014.02); *A61M 16/0875* (2013.01); *A61M 16/1095* (2014.02); *A61M 16/16* (2013.01); *A61M 2016/0027* (2013.01); *A61M 2016/0033* (2013.01); *A61M 2205/3569* (2013.01); *A61M 2205/3592* (2013.01); *A61M 2205/42* (2013.01); *A61M 2205/50* (2013.01)

(58) Field of Classification Search
   CPC .......... A61M 2205/50; A61M 16/0816; A61M 16/1095; A61M 2205/42; A61M 16/0066; A61M 16/0672; A61M 16/06; A61M 16/08; A61M 16/0825; A61M 16/0875; A61M 16/201; F16K 11/072; F16K 11/0873; F16K 5/0407; F16K 11/087; F16K 5/06; A61B 5/08–5/09
   USPC ..... 251/129.14, 315.01, 315.16; 128/201.28, 128/205.24, 206.14, 207.16
   See application file for complete search history.

(56) References Cited

U.S. PATENT DOCUMENTS

| | | | |
|---|---|---|---|
| 3,431,931 A * | 3/1969 | Cupp | ................ A62B 9/02 128/207.12 |
| 3,431,932 A * | 3/1969 | Cupp | ................ A62B 9/02 128/207.12 |
| 3,985,334 A | 10/1976 | Domyan | |
| 4,094,492 A | 6/1978 | Beeman et al. | |
| 4,796,619 A | 1/1989 | Walther | |
| 4,842,245 A | 6/1989 | Kelsey | |
| 5,193,529 A * | 3/1993 | Labaere | ................ A63B 23/18 128/200.24 |
| 5,370,154 A | 12/1994 | Greer | |
| 5,568,910 A | 10/1996 | Koehler et al. | |
| 5,918,597 A | 7/1999 | Jones et al. | |
| 6,006,748 A | 12/1999 | Hollis | |
| 6,182,656 B1 | 2/2001 | Sagiv | |
| 6,446,629 B1 * | 9/2002 | Takaki | ............... A61M 16/0096 128/204.18 |
| 6,543,449 B1 | 4/2003 | Woodring et al. | |
| 6,581,594 B1 | 6/2003 | Drew et al. | |
| 6,581,596 B1 | 6/2003 | Truitt et al. | |
| 6,659,101 B2 | 12/2003 | Berthon-Jones | |
| 6,708,690 B1 | 3/2004 | Hete et al. | |
| 6,722,359 B2 | 4/2004 | Chalvignac | |
| 6,752,150 B1 | 6/2004 | Remmers et al. | |
| 7,073,501 B2 | 7/2006 | Remmers et al. | |
| 8,251,066 B1 * | 8/2012 | Ho | ................. A61M 16/06 128/204.18 |
| 8,366,645 B1 | 2/2013 | Belalcazar | |
| 2003/0000532 A1 | 1/2003 | Bowman et al. | |
| 2003/0075176 A1 | 4/2003 | Fukunaga et al. | |
| 2004/0007232 A1 | 1/2004 | Rochat | |
| 2004/0144383 A1 | 7/2004 | Thomas et al. | |
| 2005/0126648 A1 | 6/2005 | Vu et al. | |
| 2006/0060200 A1 | 3/2006 | Ho et al. | |
| 2006/0060245 A1 | 3/2006 | Baumgarten et al. | |
| 2006/0090762 A1 | 5/2006 | Hegde et al. | |
| 2007/0033793 A1 | 2/2007 | Schlosser et al. | |
| 2008/0000472 A1 * | 1/2008 | Wall | ................. A61M 16/20 128/202.27 |
| 2008/0047560 A1 | 2/2008 | Veliss et al. | |
| 2008/0060656 A1 | 3/2008 | Isaza | |
| 2008/0169443 A1 | 7/2008 | Loloff | |
| 2008/0283060 A1 | 11/2008 | Bassin | |
| 2008/0302364 A1 | 12/2008 | Garde et al. | |
| 2009/0260631 A1 | 10/2009 | Aubonnet et al. | |
| 2010/0043796 A1 | 2/2010 | Meynink et al. | |
| 2010/0258123 A1 | 10/2010 | Somaiya et al. | |
| 2010/0307500 A1 | 12/2010 | Armitstead | |
| 2010/0318039 A1 | 12/2010 | Hall et al. | |
| 2010/0326447 A1 | 12/2010 | Loomas et al. | |
| 2011/0126832 A1 | 6/2011 | Winter et al. | |
| 2011/0126834 A1 | 6/2011 | Winter et al. | |
| 2011/0127339 A1 | 6/2011 | Li et al. | |
| 2013/0102917 A1 | 4/2013 | Colbaugh et al. | |
| 2015/0136137 A1 * | 5/2015 | Bugamelli | .......... A61M 16/208 128/205.24 |

FOREIGN PATENT DOCUMENTS

| | | |
|---|---|---|
| EP | 1197238 A2 | 4/2002 |
| EP | 1327458 A1 | 7/2003 |
| EP | 1923088 A2 | 5/2008 |
| FR | 2 784 587 A1 | 4/2000 |
| JP | 2003511160 A | 3/2003 |
| JP | 2006513004 A | 4/2006 |
| JP | 2007512047 A | 5/2007 |
| WO | 9014121 A1 | 11/1990 |
| WO | 0126722 A1 | 4/2001 |
| WO | 2002/053217 | 7/2002 |
| WO | 2004069317 A1 | 8/2004 |
| WO | 2005047797 A2 | 5/2005 |
| WO | 2005/051468 | 6/2005 |
| WO | 2006/102708 A1 | 10/2006 |
| WO | 2008/055308 | 5/2008 |
| WO | 2011006199 A1 | 1/2011 |
| WO | 2011144541 A1 | 11/2011 |
| WO | 2012012835 A2 | 2/2012 |
| WO | 2013040198 A2 | 3/2013 |

OTHER PUBLICATIONS

Partial European Search Report for Application No. 13183779.1 dated Dec. 11, 2013.
U.S. Appl. No. 61/226,069, filed Jul. 16, 2009.
U.S. Appl. No. 61/369,247, filed Jul. 30, 2010.
International Search Report and Written Opinion for Application No. PCT/US2012/055148 dated Feb. 15, 2013.
European Search Report for Application No. EP12831096 dated Feb. 17, 2015.

* cited by examiner

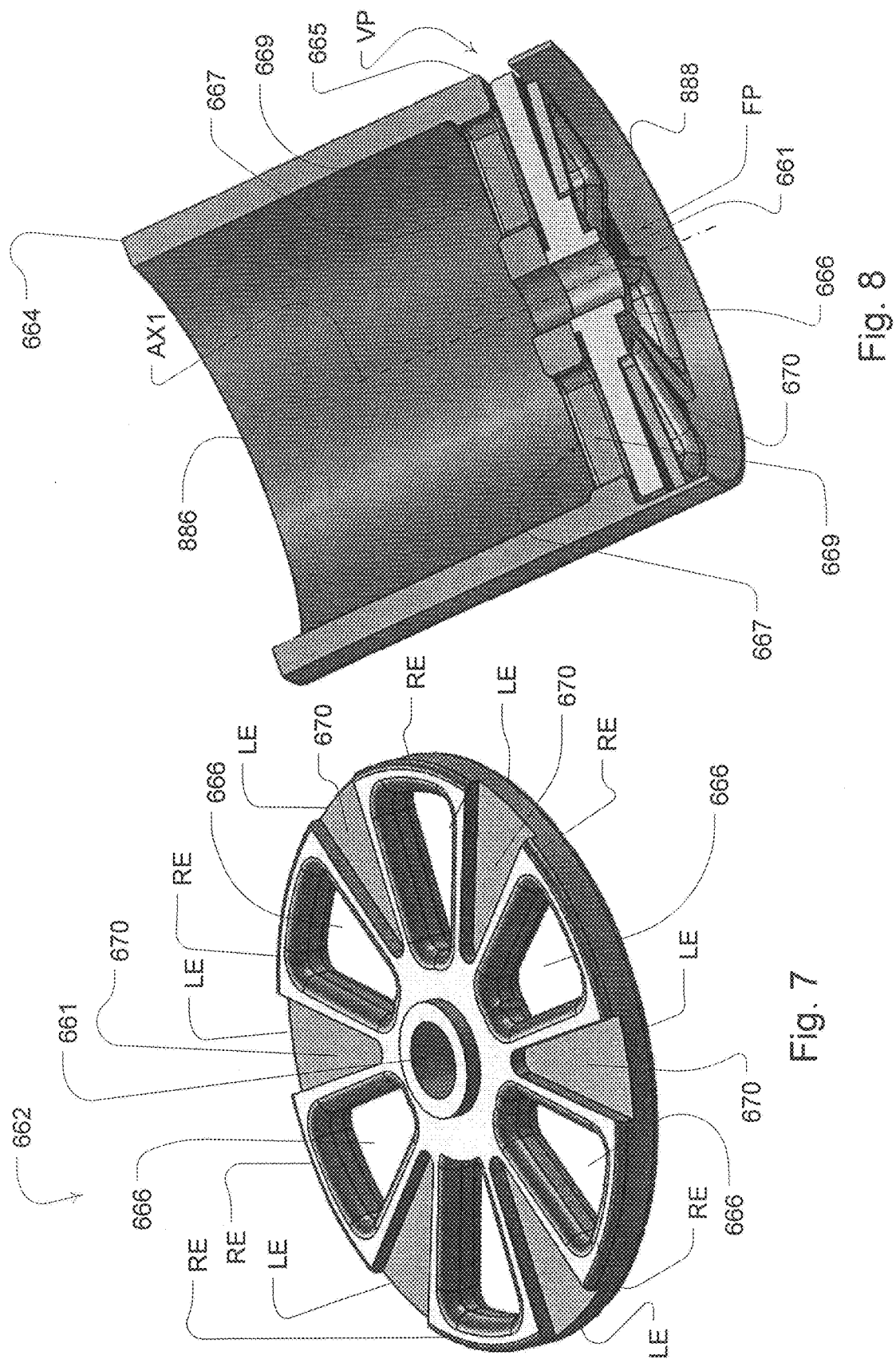

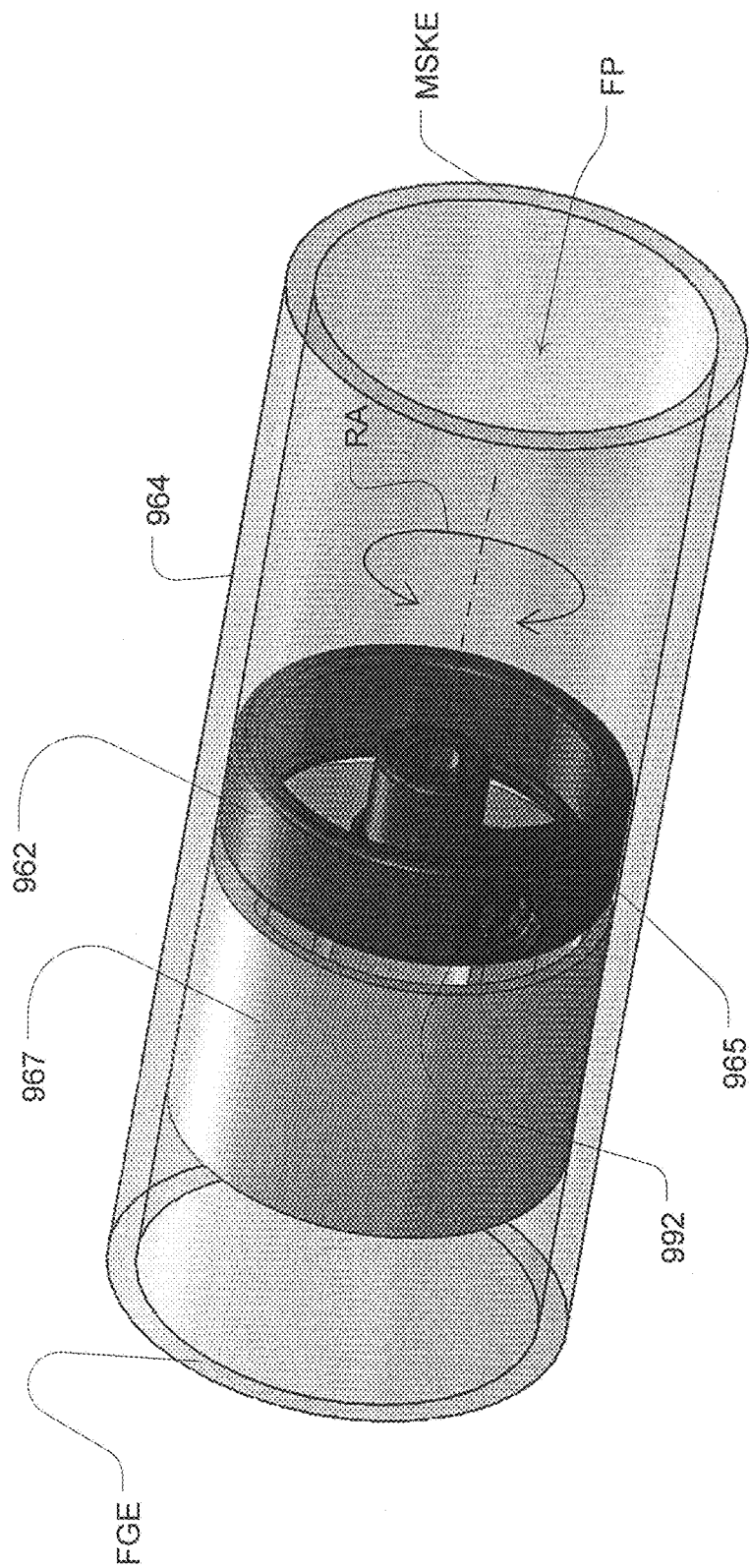

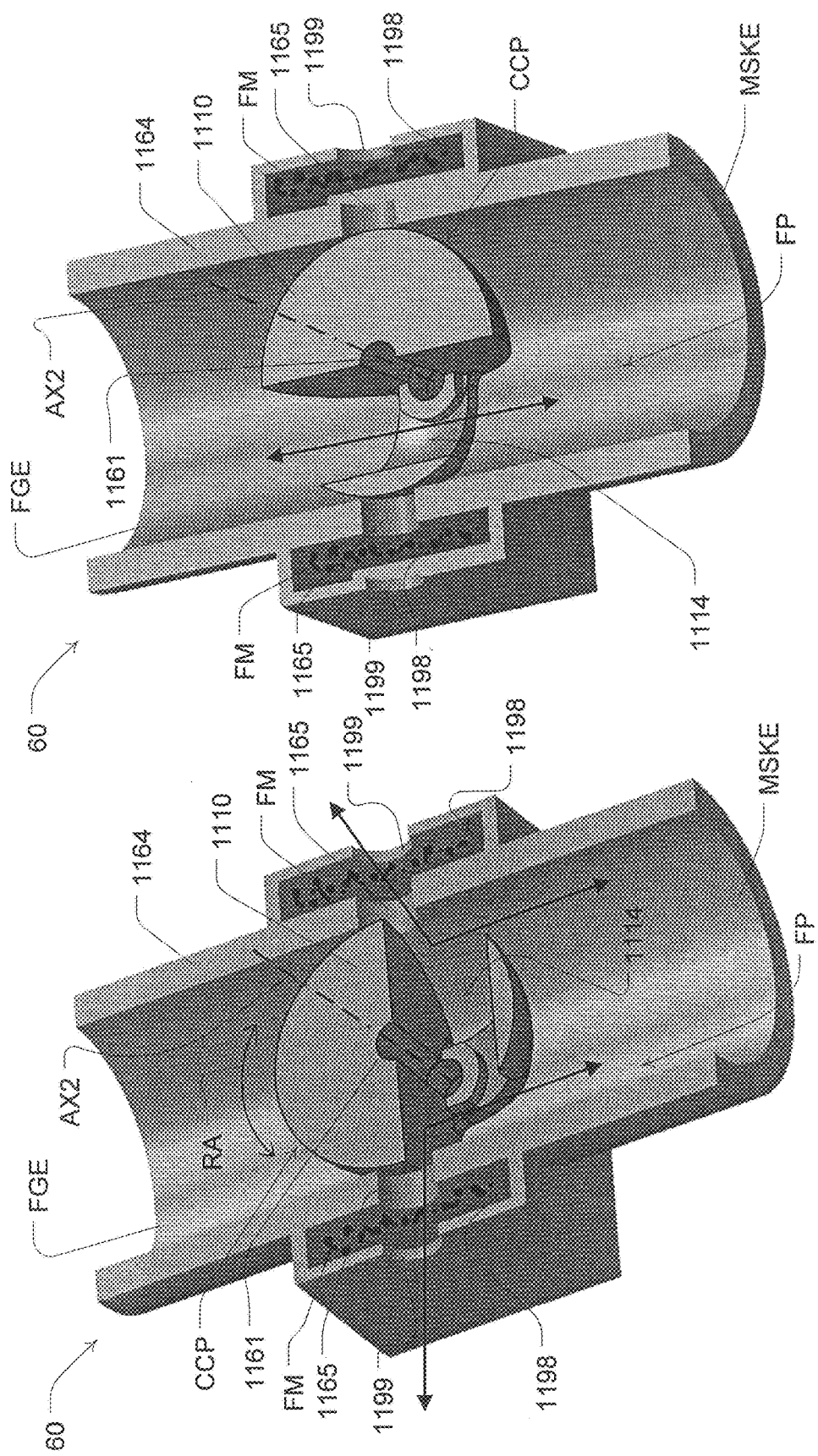

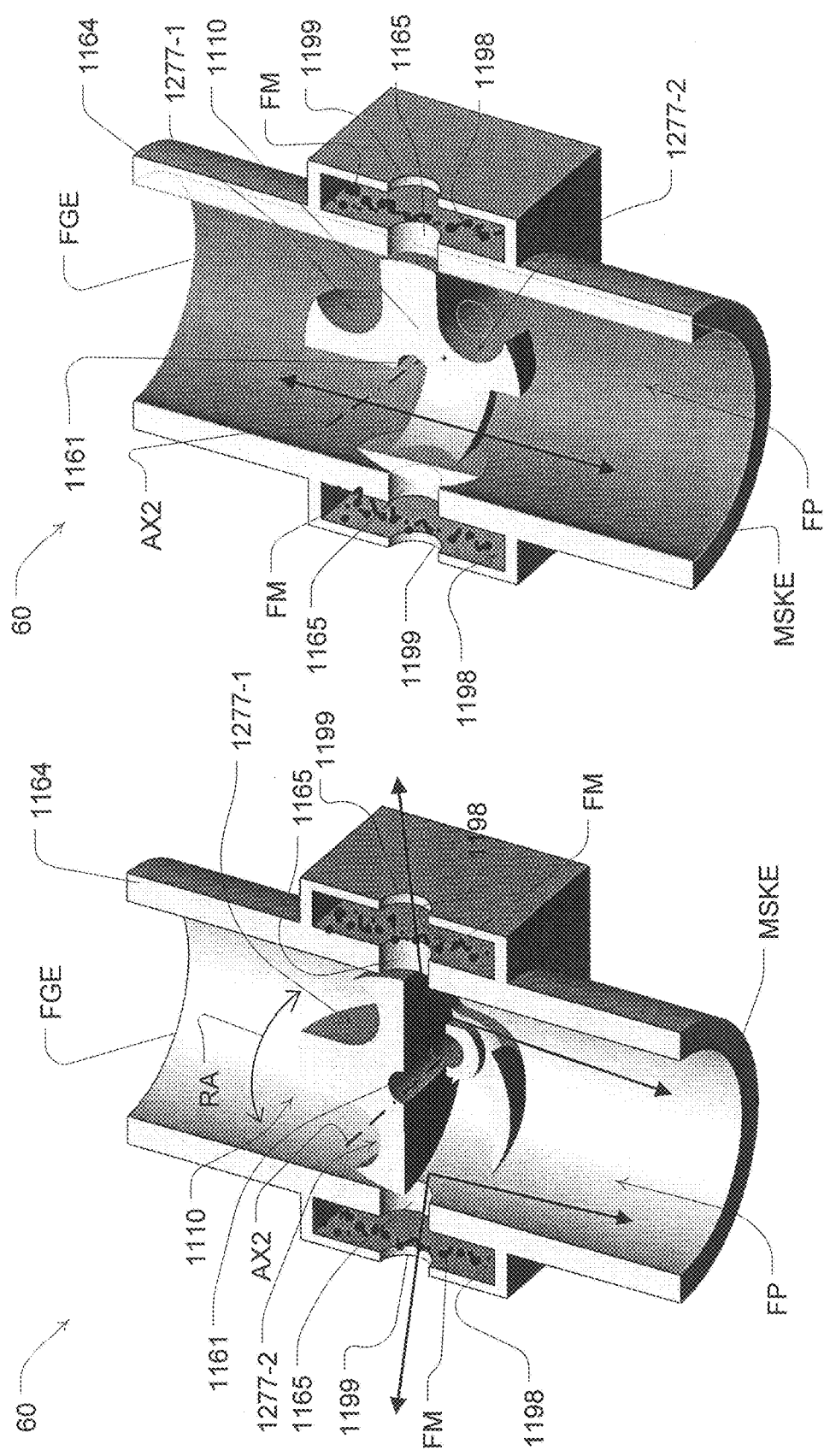

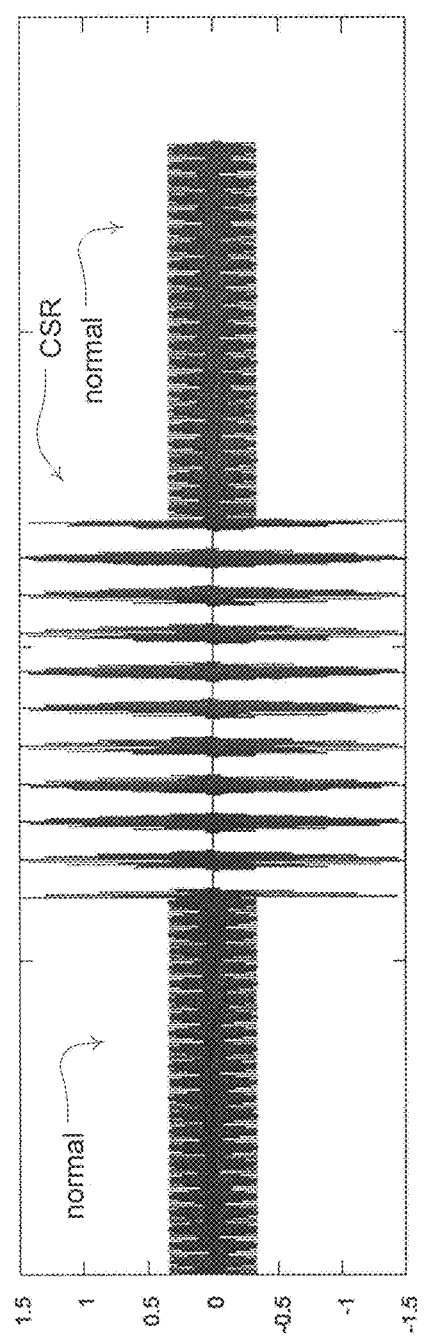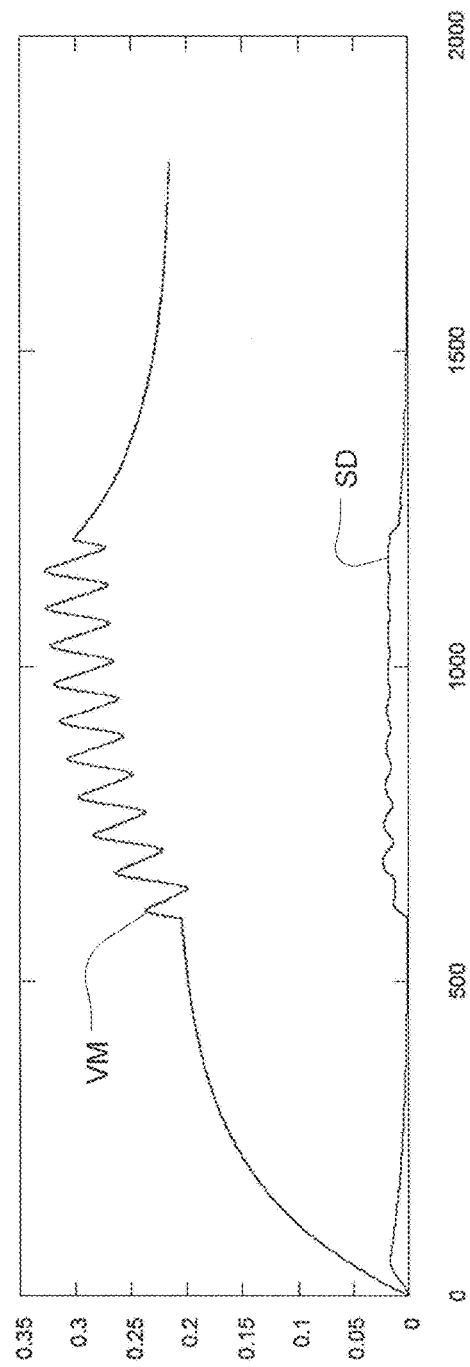

VENT ARRANGEMENT FOR RESPIRATORY MASK

CROSS REFERENCE TO RELATED APPLICATIONS

The present application claims the benefit of the filing date of U.S. Provisional Patent Application No. 61/699,520 filed Sep. 11, 2012, the disclosure of which is hereby incorporated herein by reference.

FIELD OF THE TECHNOLOGY

The present technology relates to conduits for a respiratory treatment apparatus such as a vent arrangement for a mask assembly that may be implemented for a respiratory pressure treatment including, for example, Non-invasive Positive Pressure Ventilation (NPPV) and continuous positive airway pressure (CPAP) therapy of sleep disordered breathing (SDB) conditions such as obstructive sleep apnea (OSA).

BACKGROUND OF THE TECHNOLOGY

Treatment of sleep disordered breathing (SDB), such as obstructive sleep apnea (OSA), by a respiratory treatment apparatus such as a continuous positive airway pressure (CPAP) flow generator system involves a delivery of air (or other breathable gas) at pressures above atmospheric pressure to the airways of a human or other mammalian patient via a conduit and/or a mask. Typically, the mask fits over the mouth and/or nose of the patient, or may be an under-nose style mask such as a nasal pillows or nasal cushion style mask. Pressurized air flows to the mask and to the airways of the patient via the nose and/or mouth. As the patient exhales, carbon dioxide gas may collect in the mask. A washout vent in the mask or conduit may be implemented to discharge the exhaled gas from the mask to atmosphere.

The washout vent is normally located in the mask or substantially near the mask in a gas delivery conduit coupled to the mask. The washout of gas through the vent to the atmosphere removes exhaled gases to prevent carbon dioxide build-up. "Rebreathing" of exhaled carbon dioxide may be a health risk to the mask wearer. Adequate gas washout may be achieved by selecting a vent size and configuration that allows a minimum safe washout flow at a low operating CPAP pressure, which typically can be as low as 4 cm $H_2O$ for adults and 2 cm $H_2O$ for children.

WO 2006/102708 describes an air delivery system with a vent valve that is controlled to maintain a substantially constant air flow in the air delivery conduit and the air flow generator.

WO2005/051468 describes a vent assembly for use with a mask assembly. The vent assembly includes a first vent, a second vent and a selector to switch the flow of exhaled gas from a patient between the first and second vents.

There is a need for a gas washout vent arrangement which allows for adequate venting of carbon dioxide while permitting efficient air delivery to the patient.

SUMMARY OF THE TECHNOLOGY

One aspect of the present technology relates to a washout vent arrangement for respiratory mask apparatus which incorporates a variable effective venting area or aperture(s).

Further aspects of the present technology relate to an air delivery apparatus incorporating a gas vent arrangement, and to apparatus, systems and methods for controlling variable venting of gases.

Some aspects of the present technology involve an apparatus for automated control of gas washout of a patient interface of a respiratory treatment apparatus. The apparatus may include a vent assembly having a variable exhaust area. The vent assembly may be associated with a patient interface to vent expiratory gas. The vent assembly may include a first gear having a first flow bore. The apparatus may also include an actuator to manipulate orientation of the flow bore of the first gear to vary the exhaust area.

In some cases, the apparatus may further include a second gear, the second gear may have a second flow bore. The first and second gears may be adapted in a meshed configuration. In some cases, a rotation of the first and second gears closes of the first and second flow bores to prevent a transfer of gas through a conduit of the vent assembly. In some cases, a rotation of the first and second gears opens the first and second flow bores to permit a transfer of gas through a conduit of the vent assembly. The first gear may include a set of teeth surrounding a periphery of the first gear.

Optionally, such apparatus may further include a controller including a processor. The controller may be coupled with the actuator. The controller may be configured to operate the actuator to change the exhaust area of the vent assembly. The actuator may include a motor. A shaft of the motor may be coupled with the first gear to rotate the first gear. In some examples, the apparatus may also include a position sensor. The position sensor may be configured to detect a rotational position of the first gear.

Some examples of the present technology involve an apparatus for automated control of gas washout of a patient interface of a respiratory treatment apparatus. The apparatus may include a vent assembly having a variable exhaust area. The vent assembly may be associated with a patient interface to vent expiratory gas. The vent assembly may include a radial exhaust revolver and a conduit casing. The apparatus may also include an actuator to manipulate orientation of the radial exhaust revolver to vary the exhaust area.

In some cases, the apparatus may include a radial exhaust port. The radial exhaust port may be adapted within the conduit casing of the vent assembly in which the radial exhaust revolver rotates. A peripheral edge of the radial exhaust revolver may include raised and lower edges. A proximity of a raised edge to the radial exhaust port may block at least portion of radial exhaust port. A proximity of a lower edge to the radial exhaust port may open at least portion of radial exhaust port.

In some examples, the radial exhaust revolver may include a plurality of apertures. The apertures may be adapted to permit gas flow through the revolver within the conduit casing. Optionally, the conduit casing may include a restriction element. The restriction element may be arranged with the radial exhaust revolver to selectively permit or prevent gas flow through at least one of the plurality of apertures depending on a rotational orientation of the radial exhaust revolver with respect to the restriction element. Each of the apertures of the plurality of apertures may be formed by a triangular boundary of the radial exhaust revolver. Edges of the triangular boundary of the apertures of the radial exhaust revolver may include a convex surface.

In some cases, an edge of the radial exhaust revolver may include an edge aperture. A rotational alignment of the edge aperture and the radial exhaust port may permit venting of gas from the conduit casing. In some cases, the apparatus may include a restriction element insertable within the conduit casing. The restriction element may include a flow stop and a flow aperture. Optionally, a rotational alignment position of the edge aperture and the radial exhaust port may permit venting of gas from the conduit casing. This rotational alignment position may further correspond with an alignment of the flow stop with an aperture of the radial exhaust revolver to block flow through the radial exhaust revolver and the conduit casing.

Such apparatus may further include a controller having a processor. The controller may be coupled with the actuator and be configured to operate the actuator to change the exhaust area of the vent assembly. The actuator may include a motor and a shaft of the motor may be coupled with the radial exhaust revolver. The motor may be within the conduit casing. The apparatus may also include a position sensor configured to detect a rotational position of the radial exhaust revolver.

Some examples of the present technology may involve an apparatus for automated control of gas washout of a patient interface of a respiratory treatment apparatus. The apparatus may include a vent assembly having a variable exhaust area. The vent assembly may be being associated with a patient interface to vent expiratory gas. The vent assembly may include a spherical diverter and a conduit casing. The spherical diverter may have a flow bore. The apparatus may also include an actuator to manipulate orientation of the spherical diverter to vary the exhaust area.

In some cases, rotation of the spherical diverter may position the flow bore to selectively permit a transfer of gas through the flow bore within the conduit casing of the vent assembly. A rotation of the spherical diverter may selectively position a surface of the spherical diverter to selectively block a transfer of gas through one or more exhaust ports of the conduit casing of the vent assembly. Optionally, the conduit casing may include a muffler chamber proximate to one or more exhaust ports of the conduit casing. The apparatus may also include a controller with a processor. The controller may be coupled with the actuator and configured to operate the actuator to change the exhaust area of the vent assembly. The actuator may include a motor and a shaft of the motor may be coupled with the spherical diverter. The apparatus may also include a position sensor configured to detect a rotational position of the spherical diverter.

Other aspects, features, and advantages of this technology will be apparent from the following detailed description when taken in conjunction with the accompanying drawings, which are a part of this disclosure and which illustrate, by way of example, principles of the technology. Yet further aspects of the technology will be apparent from the appended claims.

BRIEF DESCRIPTION OF THE DRAWINGS

Further example embodiments of the technology will now be described with reference to the accompanying drawings, in which:

FIG. 7 is an illustration of the exhaust revolver of the conduit vent of FIG. 6;

FIG. 8 is a cross sectional view of the conduit vent of FIG. 6;

FIG. 9 is an illustration of another example of a vent assembly implemented with a radial exhaust revolver;

FIGS. 11A and 11B are cross sectional illustrations of a conduit vent employing a spherical diverter and showing the diverter in expiratory (exhaust venting) and inspiratory (non-exhaust venting) positions respectively;

FIGS. 12A and 12B are cross sectional illustrations of a conduit vent employing a spherical diverter with J-channels and showing the diverter in inspiratory (non-exhaust venting) and expiratory (exhaust venting) positions respectively;

FIG. 15A is a graph illustrating a simulated Cheyne-Stokes breathing flow pattern;

FIG. 15B is a graph of a ventilation measure and a standard deviation SD of the ventilation measure taken from the simulated patient flow of FIG. 15A.

DETAILED DESCRIPTION

Example Respiratory Treatment Apparatus

Figure 1:
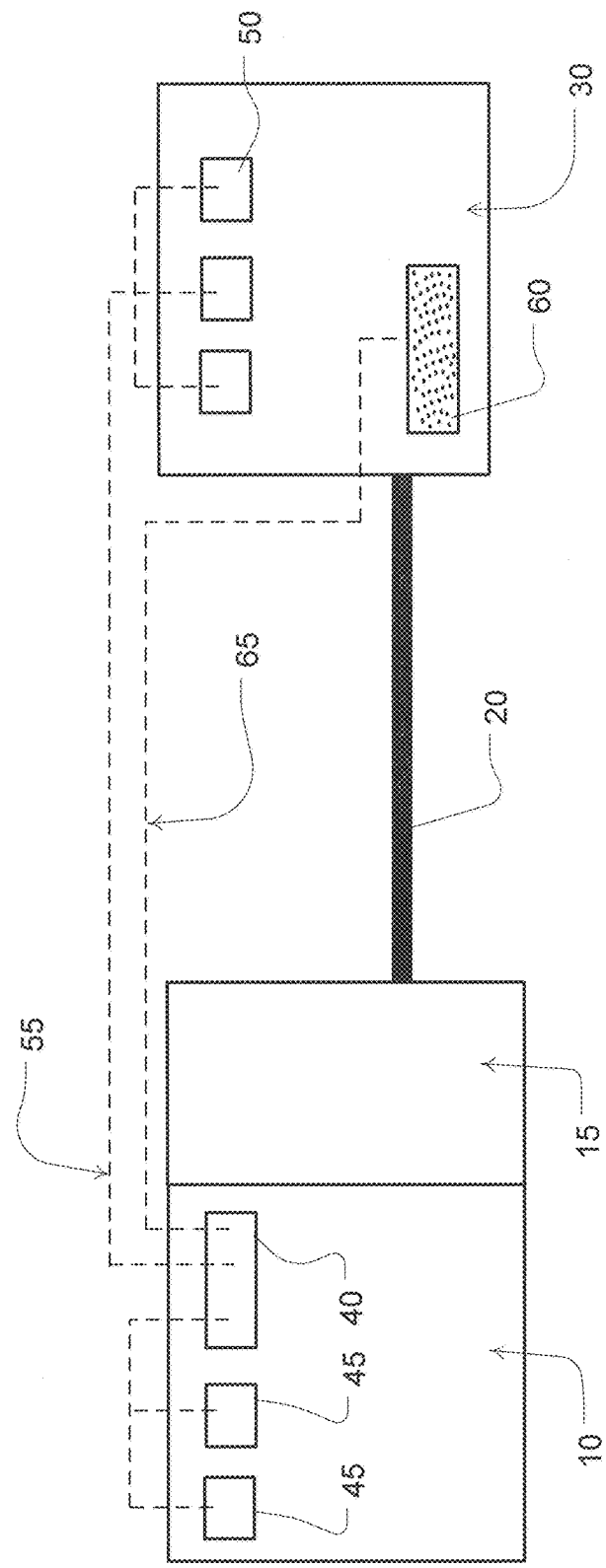
FIG. 1 is a schematic diagram of a respiratory treatment apparatus.

FIG. 1 schematically illustrates an air delivery system of a respiratory treatment apparatus for delivering breathable gas to a patient under pressure, for example, as used in CPAP therapy for sleep disordered breathing (SDB), in accordance with one example embodiment of the current technology.

The basic components of the system of FIG. 1 are an air flow generator 10, optionally a humidifier 15 which may be either integrated with or separate from the flow generator, and an air delivery conduit 20 leading from the flow generator—or from humidifier if fitted—to a patient interface 30 which is in communication with the patient's airways.

The air flow generator may be of a type generally known in the art, such as the ResMed S9™ series flow generator, and may incorporate a housing with an air inlet, a blower capable of delivering air to the patient at a pressure of, for example, 2 to 30 cm H2O, or 4 to 20 cm H2O, and an air outlet adapted for connection of air delivery conduit 20 or humidifier 15.

The flow generator may further include sensors 45, such as pressure and flow sensors, and a microprocessor control (e.g., processor 40) which may be capable of receiving signals from sensors 45 and any remote sensors 50, and to use the information from those sensors in control of the flow generator 10 and/or humidifier 15.

The air delivery conduit 20 may be a flexible tube, for example 15 or 19 mm or preferably between 8-22 mm internal diameter, for delivering the pressurized (and possibly humidified) air leaving to the patient interface 30. The conduit 20 may also incorporate one or more heating elements (not shown) for regulating temperature of the gas passing through the conduit and for preventing condensation ("rain-out") inside the tube.

The air delivery conduit 20 may also include one or more wires 55 for carrying signals to and/or from the components (e.g., remote sensors 50) located at or adjacent the patient interface 30 back to/from the processor 40. Alternatively, the signals may be multiplexed and transmitted over a heating wire of the air conduit. An example of a heated tube is disclosed in PCT application WO 2008/055308, filed 8 Nov. 2007. Still further, signals from and/or to the sensors and control components of the vent arrangements may be communicated wirelessly.

The patient interface 30 may be, for example, a nasal, pillows, prongs, cradle, full face or oro-nasal mask sealingly engaging the patient's nares, nose, and/or mouth. Examples of some of these types of mask are the ResMed Mirage Activa™, Mirage Swift™ II mask and Ultra Mirage™ masks.

In the embodiment illustrated in FIG. 1, the patient interface also includes a gas washout vent component—(schematically shown at 60), examples of which are described in more detail below. The air delivery conduit 20 may have a control wire 65 for providing signals to control the gas washout vent and/or other active components at the patient interface end of the conduit. Optionally, the control wire may also carry multiplexed signals representing measurements by sensors associated with the operation of the vent arrangements or sensors of the patient interface. In the case of the implementation of control of the movement of one or more components of the vent assembly, a controller may be configured with control instructions to implement one or more of the venting control methodologies described in International Patent Application No. PCT/US2012/055148, filed on 13 Sep. 2012 and/or Australian Provisional Patent Application No. AU 2013900885, filed on 14 Mar. 2013, the disclosures of which are incorporated herein by reference.

Alternatively, the gas washout vent assembly 60 may be positioned in the air delivery path proximal to the patient interface 30. For example, it may be positioned between the patient interface end of conduit 20 and the patient interface 30.

Alternatively, the gas washout vent assembly 60 may be displaced or positioned remote from the patient interface 30. For example, the vent assembly 60 may be positioned at the flow generator 10.

Variable Area Gas Washout Vent

In some examples of the present technology, the gas washout vent component may be a variable venting area gas washout vent and/or a variable venting rate gas washout vent. Such variable gas washout venting may have one or more of the following advantages. A fixed vent will typically require an increase in flow (and power) of the flow generator in order to increase $CO_2$ washout and a decrease in flow of the flow generator to decrease washout. However, a variable vent may increase or decrease $CO_2$ washout without such power increases or decreases simply by opening or closing the vent. Changes to $CO_2$ washout may also be made more rapidly and/or with more precision with a variable vent when compared to waiting for the flow generator to change pressure and flow to do so with a fixed vent. Moreover, when combining flow generator changes with the adjustment of a variable vent, even quicker and/or more precise adjustments to washout may be achieved. Furthermore, use of a variable mask vent can permit a patient to feel less claustrophobic since a more open vent with a greater vent flow can make a mask feel more open.

Moreover, such a vent may allow for a reduction of the flow of air to the patient. It may reduce turbulence of air and thereby decrease noise. It may also reduce turbulence in the mask to better simulate normal breathing. Alternatively, control of the vent can increase turbulence in the mask to improve venting such as for better $CO_2$ washout. It may require less power from the flow generator. It may allow for smaller flow generators and their associated components (e.g., humidifiers). It may reduce the cost of the therapy system (e.g., due to the smaller components). It may also be used to reduce the exhalation pressure which increases comfort and may thereby increase or improve $CO_2$ washout.

Apparatus Incorporating Variable Area Gas Washout Vent

Figure 2:
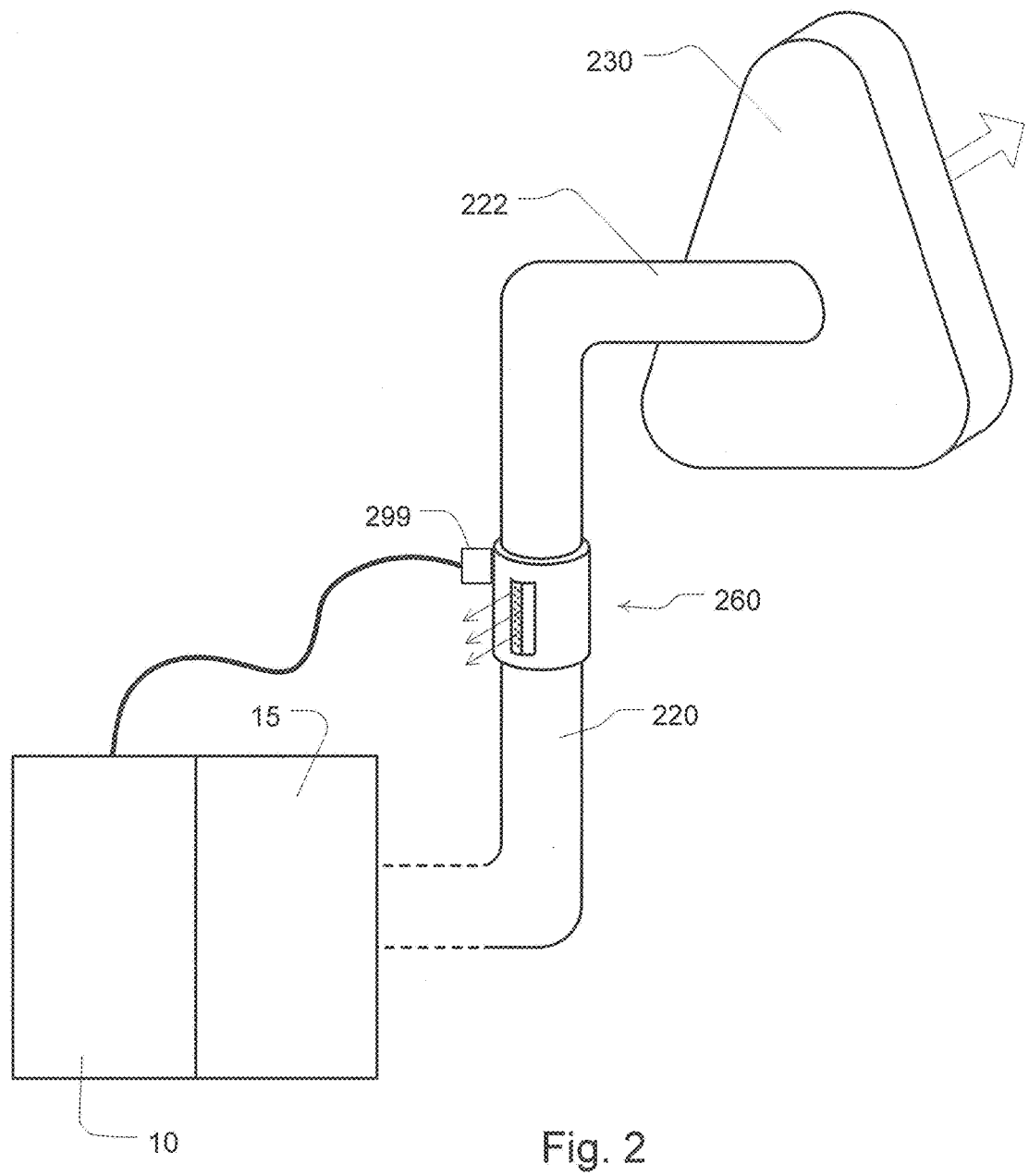
FIG. 2 shows incorporation of a variable area vent assembly into a respiratory mask and gas conduit arrangement.

FIG. 2 is a schematic illustration of one example of incorporation of a variable area gas washout vent assembly into a respiratory treatment apparatus in accordance with one aspect of the current technology.

In the arrangement of FIG. 2, the respiratory treatment apparatus includes a flow generator 10 and humidifier 15 system generally as described above for FIG. 1. An air delivery conduit 220 delivers pressurized air from the flow generator to a patient interface for applying the generated air pressure to the patient's airways. In the illustrated embodiment the patient interface is of the triangular full face or nasal type respiratory mask 230. However, other types of patient interface may be applicable.

The mask 230 includes an elbow connecting element 222 for connection of the mask to the air supply.

The gas washout vent assembly 260, generally in accordance with the embodiments described above, can be provided with one or more end connectors (not shown) for connection to the air delivery conduit 220 and the elbow connecting element 222 for location in the airway path between the air delivery conduit and the elbow so that it may be substantially near the patient interface. Alternative positions may be implemented (e.g., between the elbow and the mask.) An example actuator 299, such as a motor, solenoid or pneumatic piston, is also illustrated symbolically in the embodiment of FIG. 2. The gas washout vent assembly 260 thus allows venting of exhaled gases from the patient.

The vent assembly 260 and delivery conduit 220 may further include mating electrical connectors for power take off and conveyance of feedback and control signals, as further described below.

Figure 3:
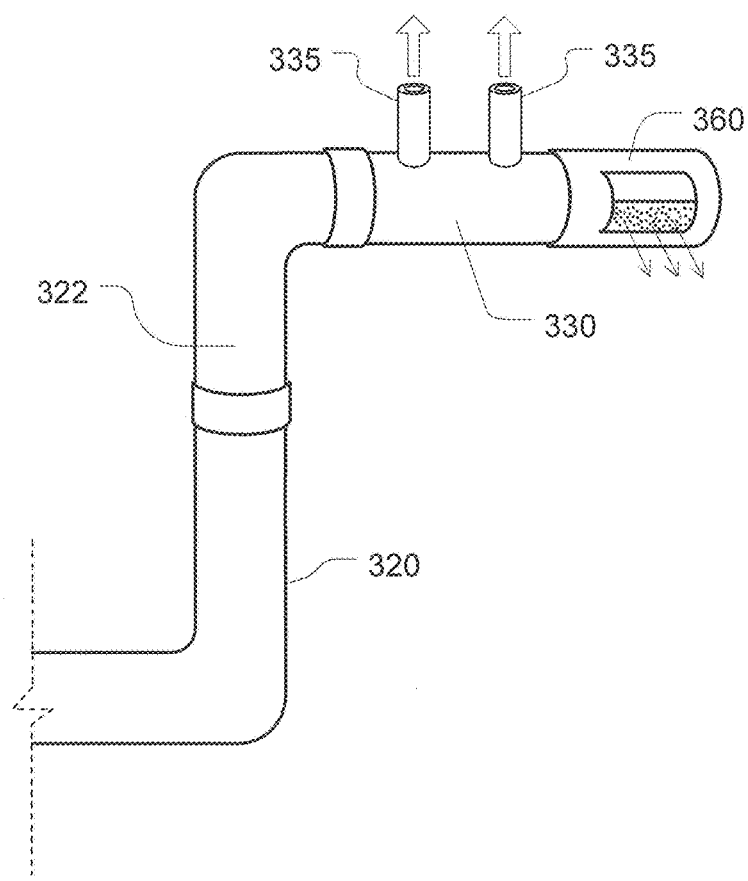
FIG. 3 shows incorporation of a variable area vent assembly into an under-nose nasal pillows style respiratory mask.

FIG. 3 illustrates a further example gas washout vent according to some examples of the current technology implemented with a respiratory treatment apparatus. In this embodiment, an under-nose patient interface, such as a nasal cushion, nasal pillows or prongs, includes the gas washout vent.

Similar to the previously described embodiments, the example of FIG. 3 includes an air delivery conduit 320 leading from a flow generator (not shown) to the patient interface 330, which in the illustrated example includes nozzles 335 for sealing against the patient's nares.

In contrast to the example of FIG. 2, in FIG. 3 the vent assembly 360 is incorporated in the patient interface 330, attached to the distal end of the patient interface 330, opposite from the pivotable elbow 322. The vent assembly 360 may take the form of any of the venting components described in more detail herein and vent the gases from the end of the assembly rather than the circumference. In some cases, an outlet muffler may be added to assist in reducing noise at the vent. For example, a tube or conduit may be added at the output of the vent to take noise further away from the mask or ears of the patient. This may also permit expired air to be channeled away from patient's face.

Example Vent Assembly Features (a) Geared Assembly Examples

Figure 4:
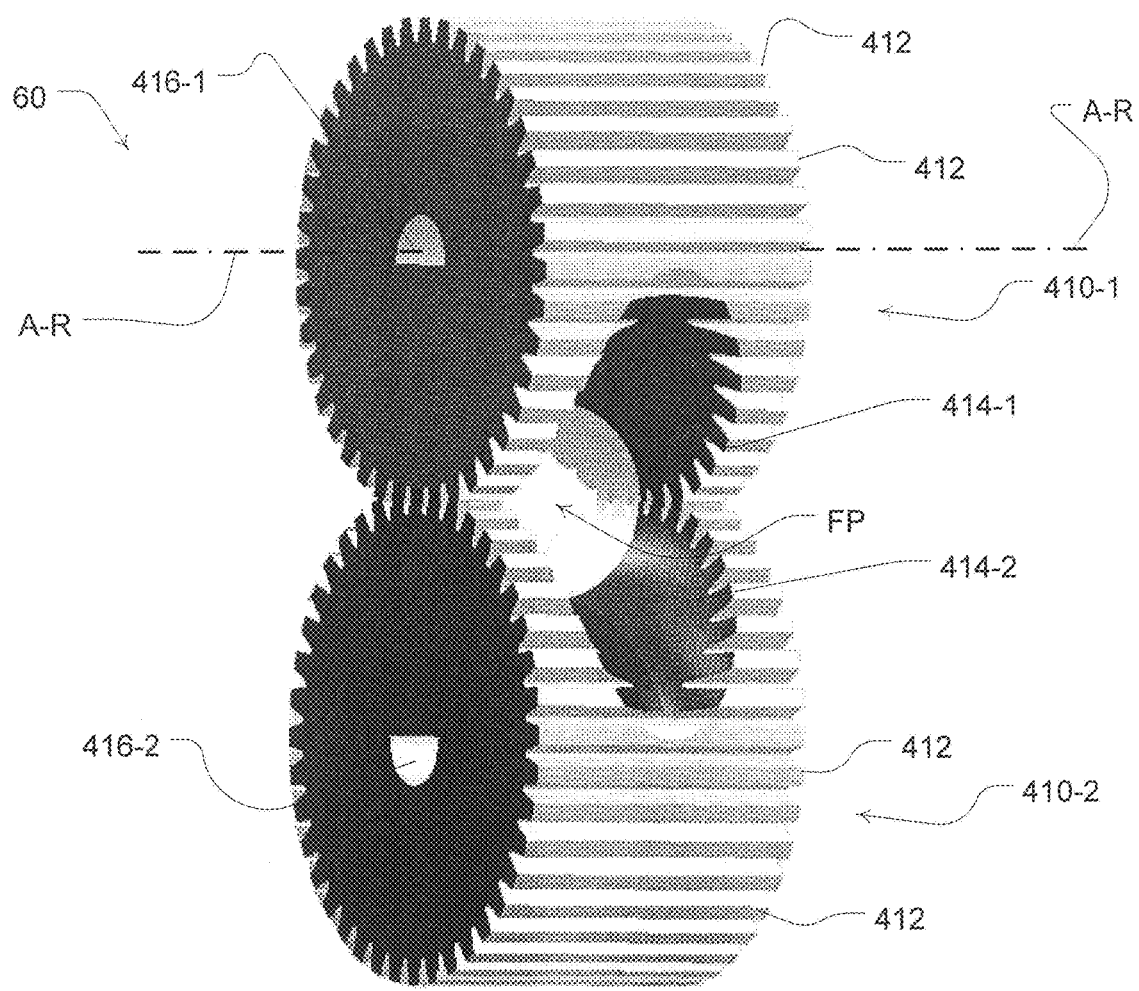
FIG. 4 is an illustration of meshed gear components for a variable area vent assembly.
Figure 5B:
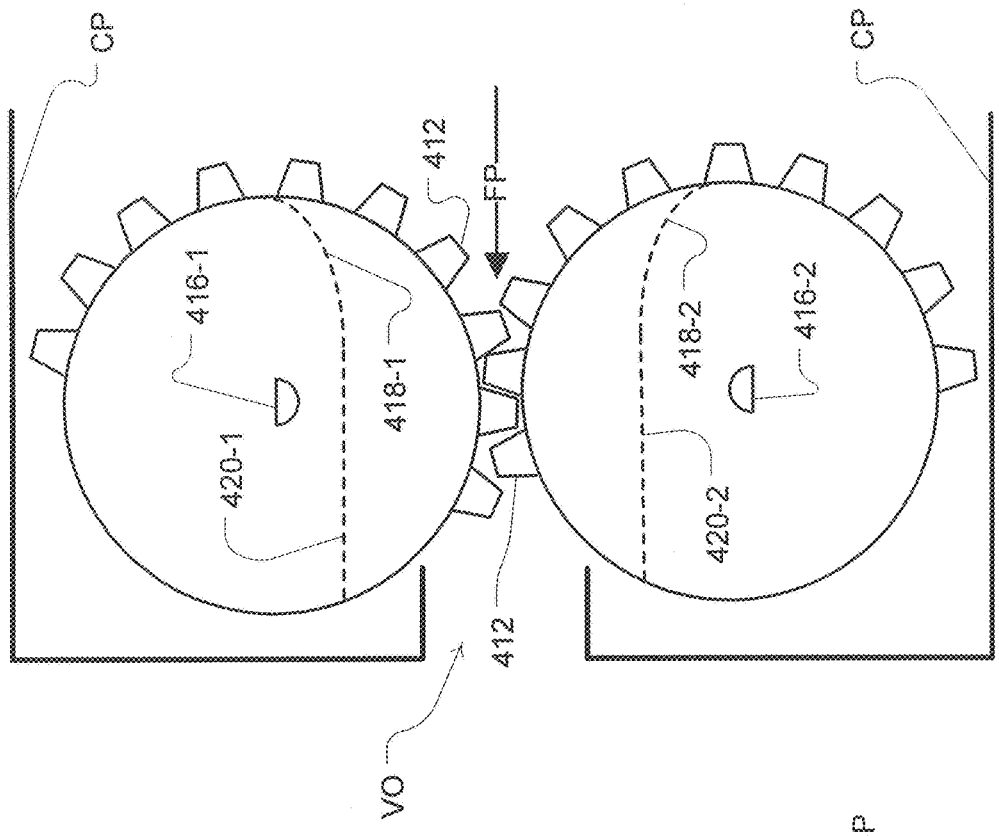
FIGS. 5A and 5B are side view illustrations of the meshed gear components of FIG. 4 in closed and open positions respectively.
Figure 5A:
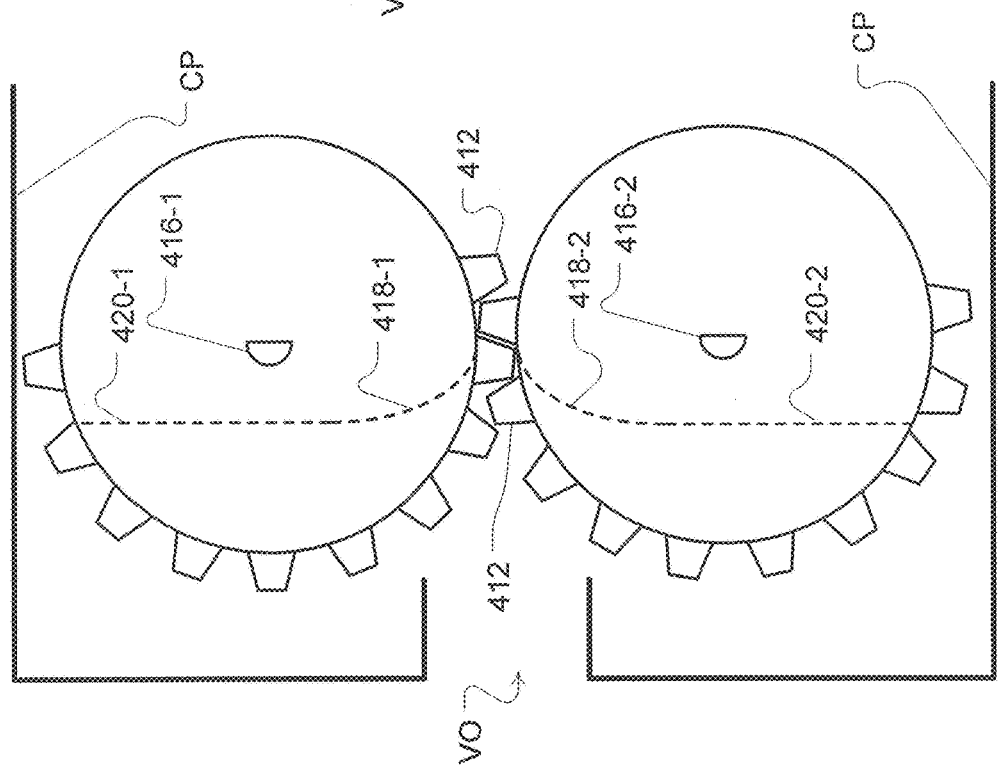

FIGS. 4, 5A and 5B show a variable vent assembly 60 in accordance with one example of the present technology. Such examples may employ one or more gears 410-1, 410-2. The gears may be integrated into a conduit passage CP that may lead to or be part of a vent as described previously. The gears may typically include gear teeth 412 around the circumference of the gear. However, fewer teeth may be implemented depending on the desired degree of rotation of each gear. One or more of the gears may also include a flow bore, the positioning of which may adjust the characteristics of the vent. As shown in the example of FIG. 4 each gear includes a flow bore 414-1, 414-2. Generally, each flow bore 414-1, 414-2 may serve as a flow passage FP through its respective gear 410-1, 410-2. The flow bore may be implemented generally perpendicular to an axis (A-R) of rotation of the gear. In this regard, one or more of the gears may include a keyed channel 416-1, 416-2 about which the gear may rotate when fitted to a rotation shaft (not shown) such as a drive shaft of a motor (e.g., a stepper motor). Such a drive shaft may have a shape to correspond to the shape of the keyed channel so that the gear may rotate with the drive shaft. Optionally, the channel of the gears may be round, rather than keyed, such that the gear may simply rotate on a fixed shaft or axle.

As illustrated in more detail in the side views of FIGS. 5A and 5B, the flow bore(s) may optionally be tapered to form a tapered portion 418-1, 418-2 that deviates from the generally straight portion 420-1, 420-2 of the flow bore. Tapering can permit different adjustments to the flow characteristics of the flow passage FP depending on the rotational positioning of the gear with respect to a conduit passage CP of the vent in which the gear is implemented.

In this regard, rotation of one or more of the gears may serve to adjust an area or size of the flow passage FP defined by the flow bore(s). For example, the rotational repositioning of the gears may be by a motor that may be external to the conduit passage CP. In the case of the implementation of two gears, the gears may be aligned in a meshed position such that the rotation of one gear rotates the other gear. In this case, only one motor can be implemented. The motor may be controlled by a controller, such as the controller of the respiratory treatment apparatus.

The rotational adjustment of the gear(s) may thereby increase or decrease area and/or rate of flow through the gear(s) emanating from a conduit passage CP to the vent opening VO past the gears. For example, as illustrated in FIG. 5A, the gears may be rotated so as to close the flow passage FP as the flow path of the flow bore is rotated to be generally perpendicular to the flow path of the conduit passage CP. In such a case the gear structure blocks the flow from the conduit passage CP. Further rotation of one or more of the gears may then permit flow through the flow passage FP as the flow path of the flow bores open when they become aligned with the flow path of the conduit passage. In the example, a rotation of ninety degrees may serve to change the flow passage FP from fully open to fully closed or from fully closed to fully open. Rotational adjustments within the range between zero and ninety degrees may permit varying degrees of flow through the flow passage FP since the flow path will be partially closed or partially open to some degree. However, depending on the configuration of the flow bore(s), other ranges of rotational motion may be implemented.

The gears and any conduit in which they are implemented may be formed of any suitable material and may advantageously be formed of a moulded plastic material such as polycarbonate, nylon or porous formed plastics such as polypropylene or similar.

(b) Radial Exhaust Revolver Venting Examples

Figure 6:
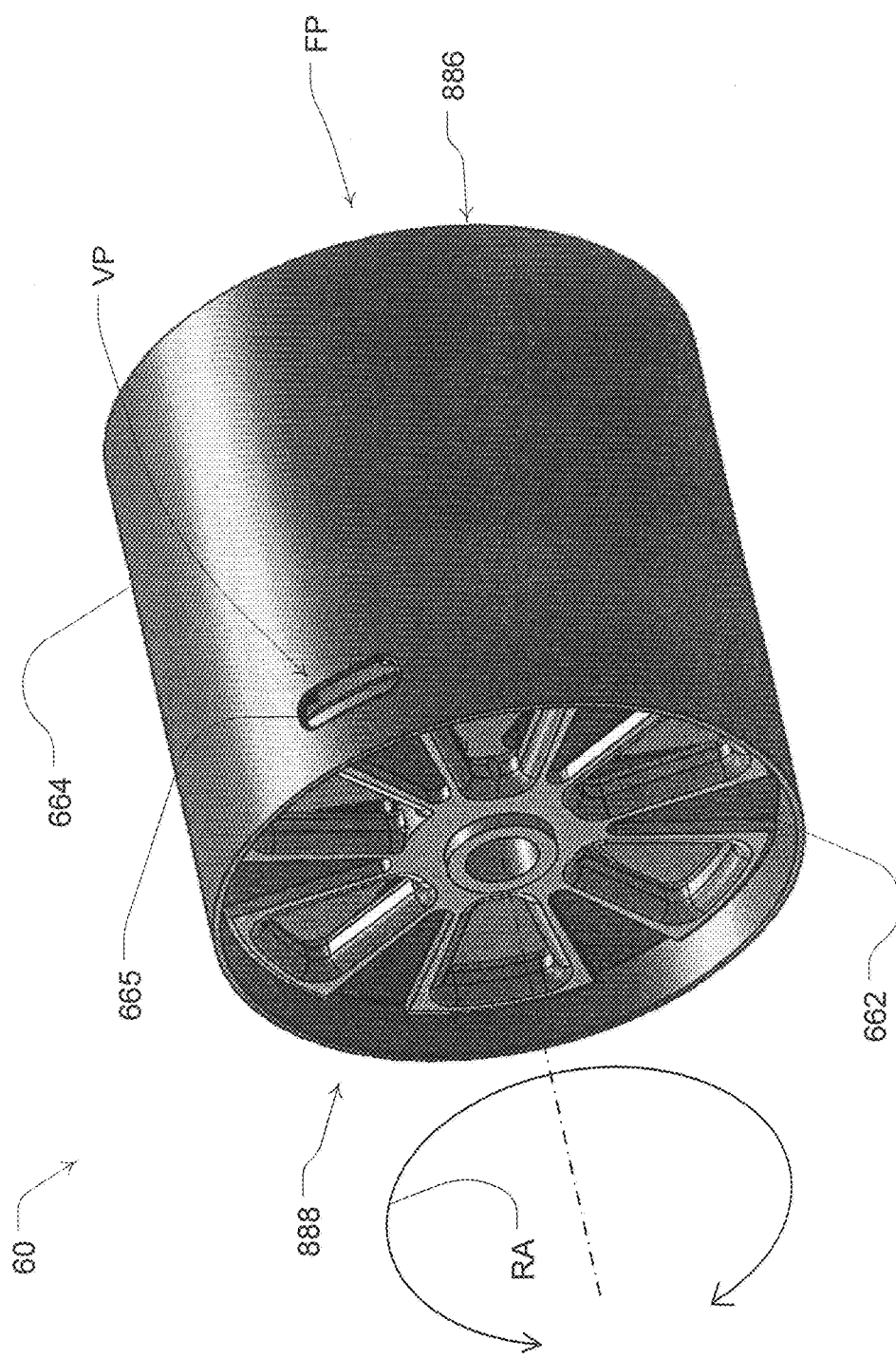
FIG. 6 is an illustration of a conduit vent of the technology including an radial exhaust revolver.

FIGS. 6, 7 and 8 provide several views of a vent assembly 60 employing a radial exhaust revolver 662. The radial exhaust revolver 662 may be inserted within a conduit casing 664, such as a cylindrical casing, that will include a flow passage FP. Air or breathable gas may be selectively vented at a radial venting portion VP at a periphery of the conduit casing 664. Such a radial venting portion may be formed by one or more side aperture(s) shown as radial exhaust port 665 on an external surface portion of the conduit casing 664 adjacent to the radial exhaust revolver 662. Typically, the conduit casing may include a flow restriction element 667 within conduit casing 664. This may be inserted or formed integrally with the conduit casing 664. The flow restriction element 667 may also be formed with one or more adjacent restriction element aperture(s) 669.

The radial exhaust revolver 662 may be inserted adjacent the flow restriction element within the conduit casing 664. In this regard, as best seen in FIG. 7, the radial exhaust revolver 662 may be formed in a circular or disk shape having one or more revolver apertures 666 and one or more revolver flow stops 670. Optionally, such apertures and stops may be triangular or other shape and they may alternate around the surface of the disk as illustrated in the example of FIG. 7. The revolver may be formed of a soft material such as a urethane material. Such a material may help to reduce operational noise of the revolver. In this regard, the inside surfaces edges of the boundary of the revolver apertures 666 may have a curved surface or other convex shape so as to avoid edges which might increase noise as gas passes through the revolver openings.

When installed, the radial exhaust revolver may be rotated, such as on an axis AX1 corresponding to shaft opening 661, in direction of arrows RA within its assembled position in the conduit casing 664. This rotation may selectively block or allow flow through the radial exhaust revolver 662 from the flow path FP of the conduit casing 664. The selective permitting of flow may be achieved when one or more restriction element apertures 669 align with one or more revolver apertures 666. The selective blocking of flow may be achieved when the revolver flow stops 670 fully align with the restriction element aperture(s) 669. A partial alignment may permit less gas flow through the revolver than when the apertures (e.g., restriction element apertures 669 and revolver apertures 666) are fully aligned.

The disk of the revolver may further include a series of raised edges RE and lowered edges LE along its periphery. Such edges may selectively align with one or more radial exhaust ports 665 so as to selectively block or permit radial exhaust through the ports. For example, when a raised edge RE revolves to be fully aligned with the exhaust port 665, no flow through the exhaust port 665 is permitted. Similarly, when a lowered edge LE revolves to be at least partially aligned with the exhaust port 665, gas of the conduit casing may vent out of the exhaust port 665. Such venting is radial or perpendicular to the axis of rotation of the revolver. The extent of the overlap of the raised edge RE with the exhaust port thereby increasing or decreasing the passable area of the exhaust port can permit varying degrees of exhaust through the port. The extent of this overlap may be controlled by controller setting the rotational position of the revolver.

Such a revolver when inserted in or between a patient interface or delivery conduit may then serve as a variable area vent. For example when the shaft of a motor (not shown), such as a stepper motor, is in the conduit casing and coupled to the revolver, the revolver may be selectively controlled by a controller of a respiratory apparatus to rotate the revolver to any desired position. In such a case, the first end 886 of the conduit casing may be coupled with an output of a flow generator or delivery conduit and the second end 888 may be coupled with a mask, such as a full face or nasal mask. The revolver may be rotated, such as during detected patient inspiration, to a position to permit flow through the conduit casing and through the revolver so that a pressurized flow from the flow generator may reach the patient at the mask. In such a position, the exhaust port 665 of the casing may be substantially or fully blocked by the revolver edge. The revolver may be further rotated, such as during detected patient expiration, to a position to reduce or prevent flow through the conduit casing and revolver so that a pressurized flow from the flow generator is reduced at the patient mask. In such a position, the exhaust port 665 of the casing may be substantially or partially open to varying degrees by the movement of the revolver edge to permit radial exhaust venting of gas through the conduit casing from the patient mask.

Another example radial exhaust revolver 962 may be considered in reference to FIGS. 9, 10 and 11. The radial exhaust revolver 962 may be installed for rotation in direction of rotation arrows RA in a conduit casing 964 for variable venting. The conduit casing 964 further includes an insertable flow restriction element 967. However, such an element may be integrated with the form of the conduit casing 964. Radial venting is permitted when one or more radial apertures 992 of the revolver 962 align with the exhaust port 965 of the conduit casing 964. Gas flow through the conduit is permitted when the revolver 962 rotates, such as a shaft (not shown) of shaft opening 961, to align revolver aperture 966 with restriction element aperture 969.

Figure 10A:
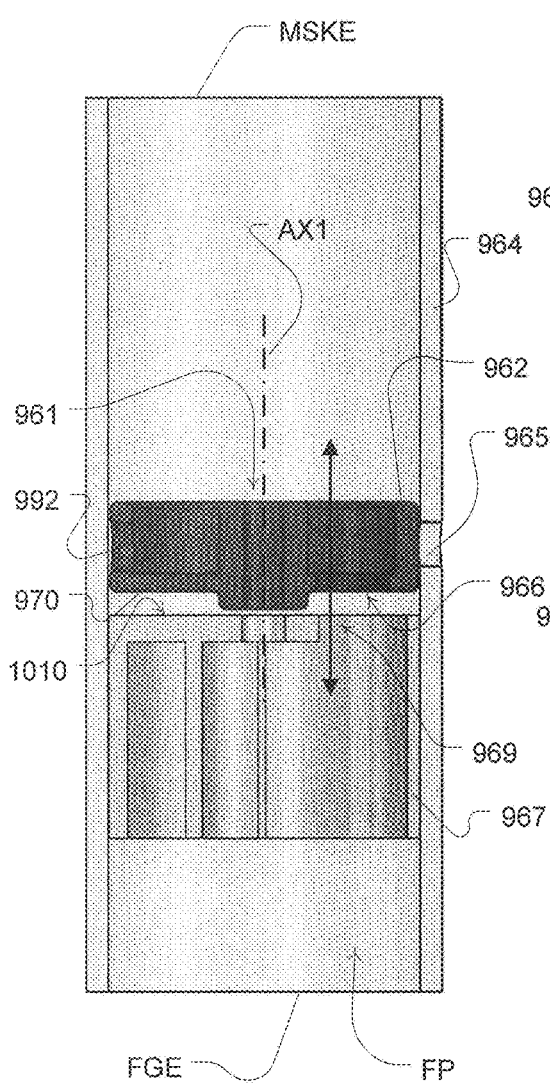
FIGS. 10A and 10B are cross sectional illustrations of the conduit vent of FIG. 9 with the radial exhaust revolver in inspiratory (non-exhaust venting) and expiratory (exhaust venting) positions respectively.

For example, as shown in FIG. 10A, the conduit casing 964 may be coupled to a respiratory apparatus so as to have a flow generator end FGE and a mask end MSKE. When the revolver edge aperture 992 at the edge of the revolver rotates to be aligned with a wall portion of the conduit casing 964 as seen in FIG. 10A, no radial exhaust venting is permitted. In this position, a pressurized flow of breathable gas from the flow generator end FGE of the conduit casing passes through the revolver aperture 966 that is aligned with the restriction element aperture 969 toward the mask end MSKE.

Figure 10B:
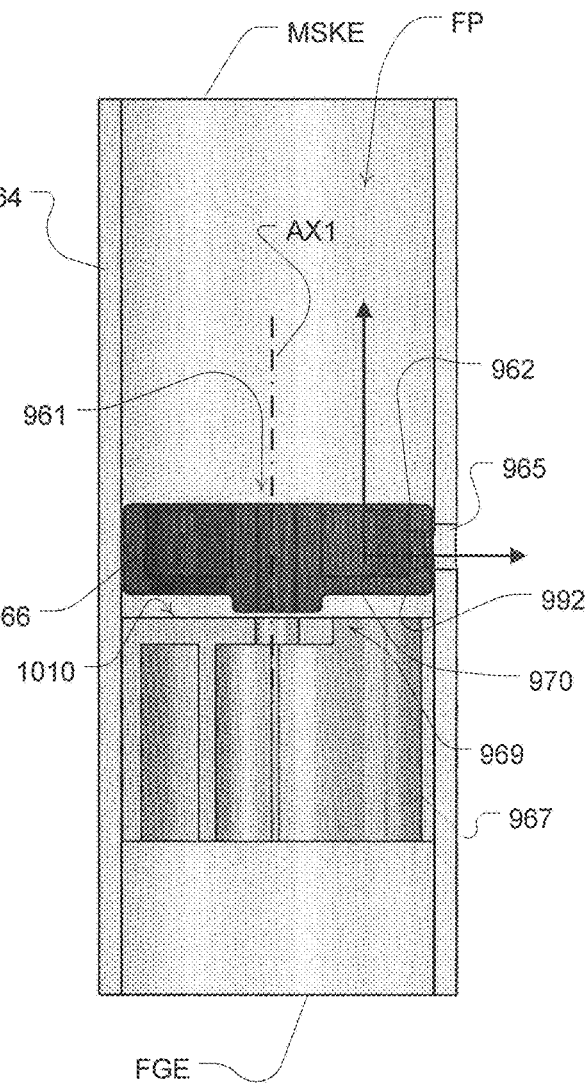

When the revolver edge aperture 992 at the edge of the revolver rotates to be aligned with the exhaust port 965 of the conduit casing 964 as seen in FIG. 10B, radial exhaust venting is permitted. In this position, no flow through the revolver aperture 966 or restriction element aperture 969 is permitted since the flow stop 970 of the revolver blocks the restriction element aperture 969 and a restriction wall 1010 surface of the flow restriction element 967 blocks the revolver aperture 966. In this position, an expiratory exhaust flow of gas from the mask end FGE of the conduit casing passes through the revolver edge aperture 992 and the aligned exhaust port 965 to vent from the conduit casing. Such a position may permit air from patient expiration to be vented from the conduit casing via the exhaust port 965 such as when the motor coupled to the revolver rotates the revolver to the position via control of a controller that detects expiration.

Depending on the size of the exhaust port or exhaust ports that are adjacent to the revolver aperture, the venting area may be varied. For example, multiple ports, such as with different port sizes, may be implemented in the conduit casing to permit variable area venting or other proportional flow venting. In such a case, the revolver aperture may be positioned adjacent to a larger exhaust port area for more venting flow or a smaller exhaust port area for less venting. In some cases, the revolver may be equipped with a position sensor to provide positioning feedback for feedback control of the revolver. For example, the revolver may be equipped with a reflective surface for a photo transistor/diode to generated a position feedback signal for a controller. Other position sensors may also be implemented. For example, one or more Hall Effect sensors may be implemented for sensing the position of the revolver.

(c) Spherical Diverter Examples

FIGS. 11A and 11B illustrate a variable area vent assembly 60 in accordance with another example. In this example a spherical diverter is employed. The flow diverter may be rotatable about an axis AX2 to selectively permit, prevent or otherwise variably adjust venting area with respect to the exhaust ports 1165 on a conduit casing 1164 (shown as a cross sectional half of the assembly). Although not shown, the axis AX2 may represent a pin or other shaft through shaft opening 1161. Rotation of the pin or shaft may thereby rotate the spherical diverter in a direction as illustrated with respect to directional arrows RA. The spherical diverter 1110 includes a flow bore 1114 through the spherical diverter. Depending on the position of the surface portions of the spherical diverter 1110, different pathways through or from the conduit casing may be blocked or partially blocked by the surface portions.

Thus, the flow bore 1114 may serve to channel gas flow through the conduit casing from a flow generator end FGE of the conduit casing 1164 to the patient interface or mask end MSKE of the conduit casing 1164 as illustrated in FIG. 11B. In this case, the surface of the spherical diverter 1110 may block or partially block a gas flow path from the inside of the conduit casing through one or more of the exhaust ports 1165. Similarly, the rotational position of the spherical diverter may permit the flow bore 1114 to serve as a channel to direct gas flow from the mask end MSKE through one or more of the exhaust ports 1165 as illustrated in FIG. 11A. In this case, the surface of the spherical diverter 1110 may block a flow path through the conduit between the flow generator end FGE and the mask end MSKE.

For example, a motor or rotary solenoid coupled to a shaft of the shaft opening 1161 may be controlled by a controller to position the spherical diverter to the exhaust port open position of FIG. 11A during, for example, detected patient expiration to permit expiratory air to vent from the conduit casing. Similarly, the motor or rotary solenoid coupled to the shaft of the shaft opening 1161 may be controlled by the controller to position the spherical diverter to the exhaust port closed position of FIG. 11B during, for example, detected patient inspiration. Positions of the spherical diverter between those shown in FIGS. 11A and 11B can permit partial opening area of the exhaust ports to permit varying of the degree of exhaust venting.

In some cases, as illustrated in the example of FIGS. 11A and 11B, the conduit casing may include one or more exhaust chambers 1198 proximate to the exhaust ports 1165. The exhaust chamber may serve as a box such as for a foam material FM or other noise suppression material to reduce noise associated with gas venting from the exhaust ports 1165. In some such cases, the wall of the exhaust chamber, when exterior to the conduit casing as shown in FIGS. 11A and 11B, can include a vent opening 1199 to permit the exhaust to escape to atmosphere after traversing through the foam material FM of the exhaust chamber 1198.

The example spherical diverter embodiment of FIGS. 12A and 12B is similar in construction and operation to that of the example of FIGS. 11A and 11B respectively. However, in the example of the FIGS. 12A and 12B, the spherical diverter includes one or more J-channel or J-bore portions 1277-1, 1277-2 as opposed to the generally convex portion CCP of the spherical diverter of FIGS. 11A and 11B. The J-channel portions may be concave recesses in the spherical diverter. Such J-channel portions may create turbulence to permit the gas flow of the conduit to assist with the rotation of the spherical diverter.

Actuation of Vent Flow Adjustment

In its simplest form, the relative open, closed and partial open positions of the vent components described herein may be manipulated manually and thus allow adjustment control of the vent flow characteristics. In some embodiments, the vent may have a manual setting for the vent area which may provide a DC component (offset) to the vent flow. Fine or course adjustments to the vent flow of such a vent may then be controlled by a controller by increasing or decreasing the vent area from the manually set vent area. The adjustment of the vent area may be continuously variable depending on the relative displacement of the moveable components (e.g., diverters, revolvers and gears) of the vent assembly. For example, a retaining mechanism may be employed to permit the adjustment of these components on their respective shafts to be made by selection of a particular position from a plurality of discrete set positions. Optionally, visual markings may be employed to indicate variable vent settings based on the relative rotational positions.

The range of adjustments may be preset by the clinician, to set the variable vent characteristics in accordance with a prescription for the patient's therapy.

In some embodiments of the current technology, the vent assembly may include an actuator for adjustment of the vent characteristics.

For example, the vent assembly may be biased towards the open position, such as by means of a torsion spring, to form a normally open vent which operates also as an anti-asphyxia valve for the patient mask. Such open positions may be considered with reference to, for example, FIGS. 6, 10B, 11A, 12A. The actuator may then act against the force of the biasing means, to close the vent either fully or proportionally.

Suitable actuators may be implemented by different types of components. For example, a voice coil may serve as the actuator including linear and rotary or swing arm voice coil actuators. Alternatively, piezo actuators (both direct and/or amplified) may be implemented. Further alternatives include pneumatic actuation (including pneumatic amplification). In such embodiments, a bleed conduit from the flow generator pressure may be provided to the mask to power a piston actuator. The piston may rotate or slide the vent assembly into the desired position as controlled by the pressure applied to the bleed conduit by one or more servo-valves, proportional valves or flow control valves.

In some embodiments where a solenoid may be utilised as the actuator, a voltage may be transmitted by a controller of the flow generator to the solenoid positioned to manipulate the vent assembly such as by adjusting the rotational position of the components of the vent assembly. The voltage transmitted to the solenoid may alter the position of the solenoid and hence the position of the vent assembly. For example, a first voltage may be applied to the vent assembly to position the vent assembly at a first position (e.g., half of the vent assembly open to atmosphere). A second voltage may be applied to the vent assembly to position the vent assembly at a second position (e.g., all of the vent assembly open to atmosphere). Such adjustable positions of the vent may be discrete but they may also be continuously variable and may run between fully opened and fully closed or some other set limits there between.

In the case of an electrically powered actuator type such as voice coil or piezo actuator, the actuator may be provided with its own power source such as battery. Optionally, it may be powered by an electrical power take-off, for example, from the heating circuit of the air delivery conduit 20. The vent assembly and air delivery conduit may be formed with mating electrical connectors for this purpose. Still further, the actuator may be powered by inductive or transformer coupling.

In one example implementation of an actuator, a voice coil actuator may be configured to achieve the relative displacement of the vent assembly, such as the rotation of the structures of the gas washout vent assembly 60. For example, one or more coil wires may be attached at the outside of the conduit of FIG. 6 or 9. A magnet may be positioned in a fixed location, for example, on a portion of the radial exhaust revolver. When a voltage is applied to the wire, the magnetic forces may then cause the repositioning of the revolver and thereby change the alignments associated with the vent openings. Different positions of the revolver may be set by controlling an application of different voltages or currents to the coil or coils.

In another actuator example, an induction coil may be attached to the vent apparatus. Optionally, a motor, such as a piezo motor, may also be attached to the induction coil. Some embodiments may be implemented with just a coil and/or just a piezo motor/driver. In some cases, embodiments may be implemented without a position sensor such as by controlling a solenoid and measuring the vent flow rather than vent position. In such a case, a flow sensor may be implemented at or near the exhaust ports or venting ports of the assembly. Alternatively, embodiments may be implemented with just a motor or driver that adjusts the position of the vent.

The control signals for the adjustment of the vent may then be learned by running a 'learn' or 'initiation' cycle. Such a cycle may optionally be implemented by the controller of the flow generator. Such a system may learn the amount of power required to adjust the vent and may optionally do so without the need (or expense) for a position sensor. Such a learn cycle may be initiated at the commencement of therapy. In such a cycle, a series of voltages may be sent to the motor (e.g., modulate the voltage) to induce a series of voltages in the induction coil to cause the vent assembly to move or step through the alignment positions of the vent from completely closed to completely open. The data concerning the minimum and maximum voltages may then be recorded or saved in association with the minimum and maximum vent positions. Similarly, the minimum voltage required to initially move the vent may be recorded. Data representing voltage that is required or desired to move the vent from the minimum to maximum positions (or vice versa) may also be recorded. In the event that the current is controlled, the current required for setting the movement of the vent to any desired position associated with a particular voltage may alternatively be recorded. In setting the vent assembly for use, the controller of the flow generator may calculate the required vent flow based on the characteristics of a certain mask such as by the methods described in WO 2002/053217. Based on learned values and the known characteristics of the vent, the controller may control applying of a voltage or current to the motor or solenoid to position the vent to obtain the desired flow.

A piezo motor may be advantageous for such an embodiment as it requires lower power to run such as in the case that power is only needed to move the vent and power is not needed to oppose a biasing force to maintain the vent in a certain position. A piezo motor however may be less accurate than a biasing force and rotational solenoid actuator, as a spring and solenoid arrangement may be able to operate with more accuracy in a small stroke.

Feedback for Control of Vent Flow

The vent assembly 60 may further include one or more sensors, such as a pressure sensor or flow sensor to measure the flow or pressure for use in the control of the vent. For example, pressure of the mask may be measured and used as a function to control the vent. Similarly, flow in or through the vent may be measured and used to control the vent. Moreover, a measure of patient flow may be applied as an input to a function for making control changes to the vent. Optionally, a position sensor may be implemented to sense the relative position of the moveable component of the vent assembly. Based on one or more of such sensors, the venting characteristics of the vent may be evaluated during operation, such as by the controller or processor of the flow generator.

Communication between the processor 40 of the flow generator and the vent assembly actuator and sensors may be through dedicated wires, or alternatively may be multiplexed with other sensor wires or multiplexed with the tube heater wires or inductively coupled to the heater wires. Alternatively, communication may be by wireless communications, such as with a Bluetooth link.

In one example embodiment, the actuator assembly may also include an infrared light that pulses infrared light rays in the direction of the vent assembly. The reflectivity may be measured such as by the amplitude of the received light, which may then be implemented as an indicator of the vent position where different amplitudes are associated with different positions of the vent. Once the position of the vent assembly is known, a processor of the flow generator may be configured to calculate the pressure and/or flow at the mask and adjust the settings of the flow generator accordingly. In addition, the actuator or motor may adjust the position of the vent assembly if the flow generator calculates that an alternative vent position is required.

Control of Vent Flow

The variable area vent arrangement of the current technology may improve the control of gas washout. This, in turn, may permit improved patient treatment and/or functioning of a respiratory treatment apparatus. For example, the vent may be operated to achieve a more instantaneous response with a flow generator to conditions at the mask. It may be operated with the flow generator to achieve faster rise and fall times. In some cases, operation of the vent can permit use of a blower that operates with a single pressure while still allowing the pressure at the mask to be varied by controlling changes to the venting area. In some cases, the changes in a vent conduit impedance may also allow for an adjustment to the pressure levels in the mask. For example, the conduit embodiments of FIGS. 11B and 12B may be coupled to a mask but not the flow generator. Thus, the conduit end labeled as the flow generator end FGE may itself escape to atmosphere as an output vent rather than being coupled to the flow generator. As such, changes in the conduit impedance that may be made by manipulation of the diverter to permit either a change in impedance from the smaller exhaust ports to the larger diameter of the end FGE of the conduit can thereby change the pressure at or flow of the vent.

Figure 13A:
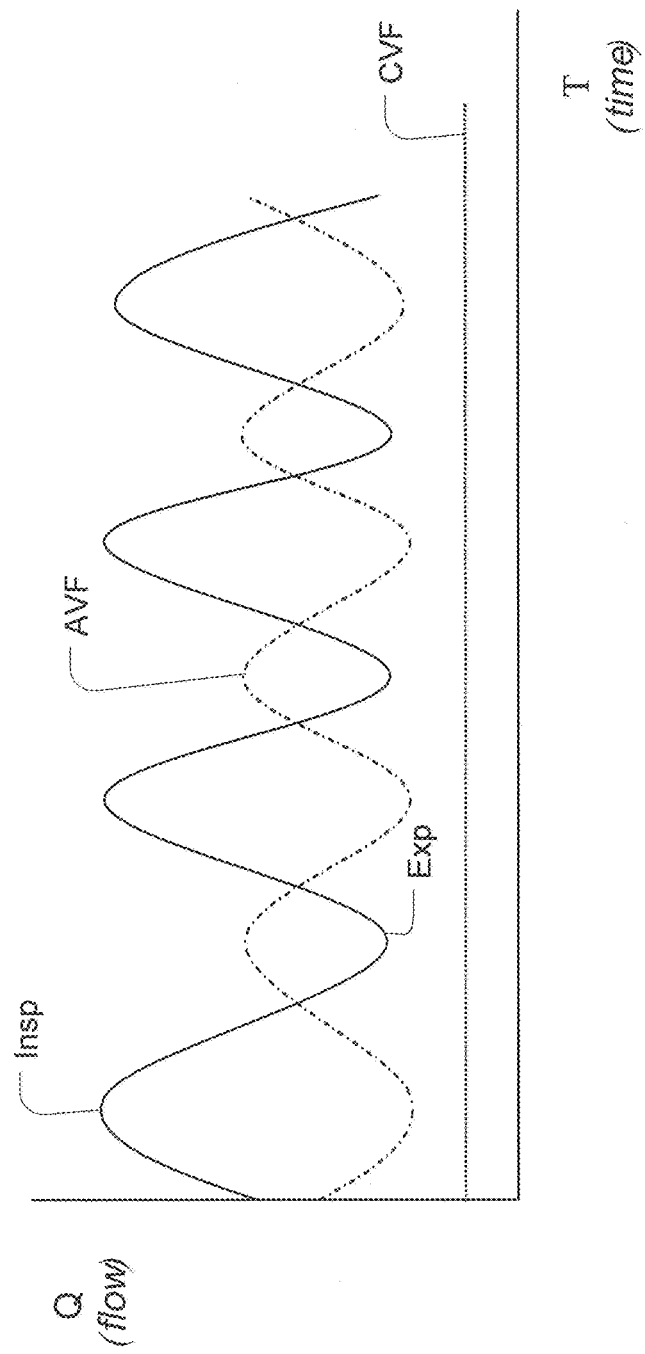
FIGS. 13A and 13B are graphs illustrating various functions for controlled vent flow verses patient respiratory flow in some embodiments.
Figure 13B:
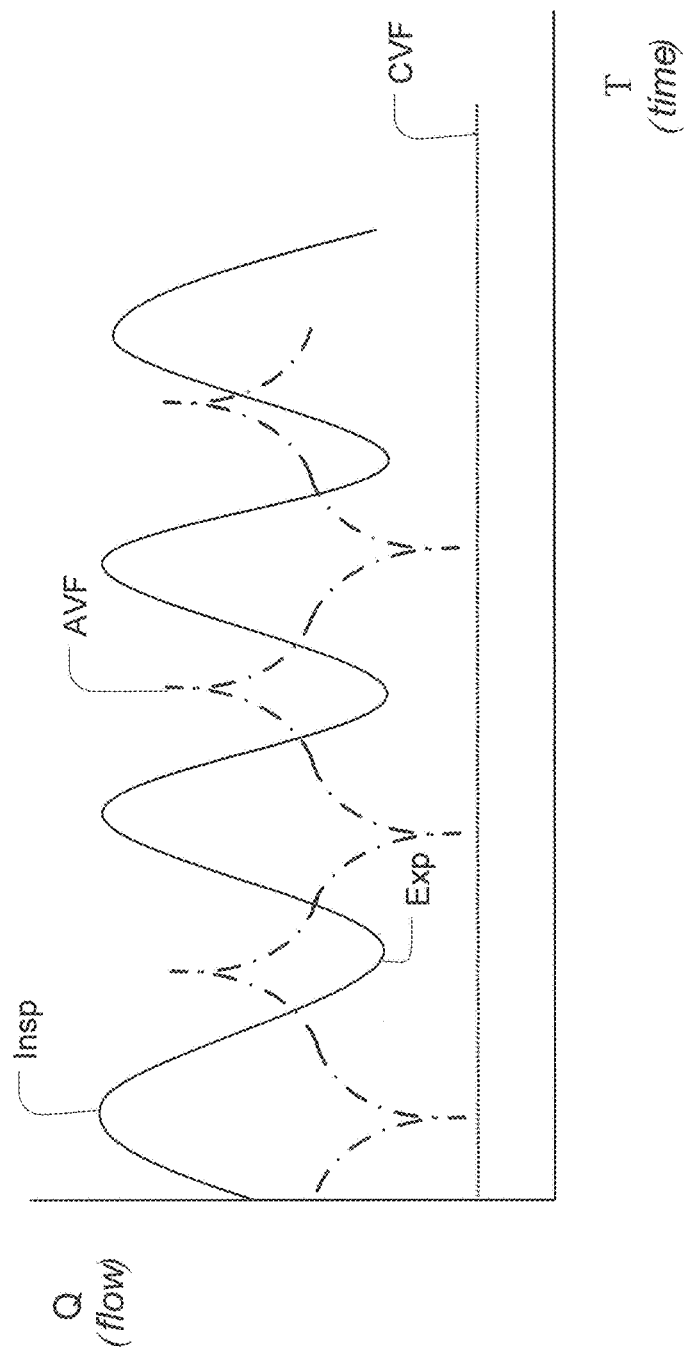

In some embodiments, control of the vent area may be implemented in synchronization with a patient's breathing cycle so as to participate in the pressure treatment of the patient. For example, the actuation of the active vent may be implemented so that the vent flow mirrors the flow of the patient's respiratory flow cycle as illustrated in FIGS. 13A and 13B. As illustrated in FIGS. 13A and 13B, the vent flow is out of phase with patient respiration. Thus, a minimal vent flow may be set for peak inspiration so that the patient may inhale more of the gases from the flow generator (as opposed to a typical non-adjustable gas washout vent where some of the gas from the flow generator passes straight out of the vent), and a maximum vent flow may be set for peak expiration. As illustrated in the graphs, different functions (e.g., sinusoidal function, shark-fin function, etc.) may be implemented for setting the change in amplitude of the vent flow. Also shown in the graph is a continuous vent flow (CVF) that could be implemented with a fixed vent or by setting the active vent to a fixed position.

Optionally, the control of the venting area and the resulting vent flow could also be phased or timed depending on the sleep state of the patient (e.g., whether they are awake, sleeping, etc.). For example, when the patient is awake (e.g., trying to get to sleep) the vent may be controlled to operate in a more open or higher flow position in cooperation with the flow generator, such as a higher flow position held approximately constant over the patient's breathing cycle, so that there is less impedance when the patient inhales. As the patient enters a sleep state, the controller of the system may then initiate operation of the vent so that it functions in the manner illustrated in FIG. 13A or 13B. Optionally, if the device then detects an awake state or non-sleep state, the vent may be controlled to return to operate in the higher flow position in cooperation with the flow generator, such as the more constant higher flow position. A determination of sleep state may be made by any suitable process but may in some embodiments be made in accordance with the sleep condition detection technologies described in PCT Patent Application No. PCT/AU2010/000894, filed on Jul. 14, 2010, the disclosure of which is incorporated herein by reference.

In some embodiments, the control of the vent could be implemented in response to detected patient conditions, such as sleep disordered breathing events. For example, an analysis of flow and/or pressure data by a processor of the controller of the flow generator may detect respiratory conditions such as central or obstructive apnea, central or obstructive hypopnea, and/or snoring etc. Example methods for detecting such conditions are described in U.S. patent application Ser. No. 12/781,070, filed on May 17, 2010, the entire disclosure of which is incorporated herein by reference. The controller may then set the vent area based on the analysis of the patient's detected condition. For example, if a central apnea is detected (an open airway apnea) or a central hypopnea, the processor may control the vent to close or reduce the vent area so that the patient is permitted to re-breath $CO_2$. This may induce the patient's brain to detect an increase in $CO_2$ in the body and thereby cause the patient to spontaneously breath. Thereafter, if the controller detects a patient's breath or if a safety time period lapses without a breath, the vent may then be controlled to return to its normal operation, such as that associated with the varied operation of FIG. 13A or 13B or a more constant open position that provides a required vent flow during respiration. Beneficially, pressure or flow adjustments that are attributable to changes of the vent area may take effect faster than such changes controlled by adjustments to some flow generators. Thus, an initial adjustment of mask conditions by manipulation of the vent may be performed before flow generator changes are implemented. This may provide the controller of the flow generator an opportunity to determine with its sensors how a patient's airway is reacting and/or how the flow generator should thereafter respond.

In one embodiment, adjustments to the venting area may be implemented to improve patient comfort or to offset a potential leak due to an improperly positioned mask. Essentially, these procedures may permit adjustments to the position of the patient's mask. For example, the controller of the flow generator may detect an occurrence of an unintentional leak that may be attributable to a displaced positioning of the mask. If such a leak is detected, the controller may control an adjustment to the vent area such as to close or rapidly close the vent assembly. Optionally, such a closing of the vent may be joined by a simultaneous controlled increase in speed of a flow generator to temporarily increase airflow or pressure delivered to the mask. The pressure increase at the mask resulting from the closing of the vent assembly may then cause the mask to 'jump', shake or disrupt from the patient's face. This jump or movement of the mask may result in the mask re-positioning its seal to the patient's face and potentially sealing the detected leak path.

As an alternative controlled approach, the controller may then control the vent arrangement to open (and/or simultaneously control a reduction in generated pressure by the flow generator) so that the pressure of the mask is substantially reduced (e.g., to a pressure or atmospheric pressure) for some predetermined period of time. This substantial reduction of pressure in the mask may then allow the mask to be re-positioned by some movement of the patient or allow the mask to change in the case of an auto adjusting mask and thereby potentially correct the seal issue. Optionally, this controlled opening approach may be implemented subsequently to a prior 'jump' attempt previously described, in the event that mask leak is still detected after the 'jump' attempt. Such controlled procedures may be repeated or performed (in any order) until the leak is no longer detected or for a predetermined number of times. Moreover, in some embodiments, both opening and closing the vent may be repeated rapidly and may coincide with the flow generator decreasing and increasing the pressure respectively. Such a shaking process may result in the mask vibrating to a degree to help in reset the mask position to rectify the detected leak.

Other vent area control procedures may also be implemented in response to leak detection, such as the detection of unintentional leak, performed by the controller. For example, in some embodiments, the degree of venting may be variably controlled as a function of a detection of unintentional leak and/or mouth leak (such as in the case of a nasal only mask). In such an embodiment, the pressure and flow output from the flow generator may be determined. Additionally, the vent leak may be calculated by sensing pressure or flow at or near the vent assembly. The difference between the air flow generated by the flow generator and the vent leak flow may be determined to be the sum of unintentional leak and mouth leak (where applicable). Mouth leak may be determined, for example, as described in U.S. Provisional Patent Application No. 61/369,247, filed 30 Jul. 2010, the entire disclosure of which is incorporated herein by reference. Thus, the unintentional leak flow may be calculated. (e.g., $Flow_{unintentional\_leak}=Flow_{total\_generated}-(Flow_{mouth\_leak}+Flow_{vent\_leak})$)

The vent area of the vent assembly may then be controlled based on such a determination of unintentional leak quantity by the processor of the flow generator. In one example, upon the flow generator processor determining increased or excessive unintentional leak, such as by a comparison of the quantified leak to a threshold that may be indicative of a required gas washout flow, the processor may control the vent actuator to reduce the vent open area, since less gas washout venting is required with increased unintentional leak at the patient's face. Similarly, if such a leak is no longer detected, the processor may thereafter control an increase to the vent open area so that the flow of the gas washout vent satisfies a required gas washout flow.

In a further example, by knowing the open area against pressure characteristic for the vent assembly, the processor may control the vent actuator based on the sensed or calculated pressure at the vent, to control the vent flow to remain constant or to follow a predetermined pattern.

In a yet further example, the venting may be controlled in response to the patient's breathing cycle or therapy need. Algorithms for determining cycling between inhalation and exhalation are known, and described for example in US Patent Application 2008/0283060, filed 21 Dec. 2006. By employing such an algorithm, the variable area vent controller may be controlled to synchronise with the breathing cycle, for example to reduce the vent open area or close the vent completely during part of the patient's breathing cycle. In one example, the vent area is reduced or closed at a time corresponding to inhalation when gas washout is not required, and is opened coinciding with patient exhalation.

By reducing gas venting during inhalation, it is believed that the mean and peak flow rate required to be generated by the flow generator may be reduced, with resultant decreases in flow generator capability and size, air delivery conduit diameter and humidifier capacity being possible. Furthermore, the power and water consumption of the apparatus may be able to be reduced.

The actuation of the active vent may be controlled by software. In some embodiments, the software may be upgradable or re-settable in accordance with particular patient's needs. For example, a patient with COPD may have a first vent flow requirement in their first year of treatment and then have a second vent flow requirement in their second year of treatment. The software may control this change of the vent flow setting according to year by checking an internal clock and adjusting the setting accordingly. Alternatively, the data of the software may be upgraded to re-program the active vent in the second year of treatment to cause the vent to achieve the second vent flow requirement. As discussed in more detail herein, controlled adjustments to the vent may also be made during a treatment session and may depend on detected patient conditions such as sleep stage or time in treatment. Moreover, vent adjustments may also optionally be made based on pulse oximeter measurements of the patient during treatment. For example, a controller may reduce vent size to cause re-breathing of $CO_2$ upon detection of higher than normal $paO_2$ measurements and/or lower than normal $paCO_2$ relative to one or more thresholds. The controller may then return the vent size for normal $CO_2$ washout when the pulse oximeter measurements normalize.

In some cases, an anti-asphyxia valve may no longer be necessary. The active vent could also serve as an anti-asphyxia valve. For example, such an embodiment may be implemented such as when the vent includes a biasing member. The biasing member may maintain the vent in a normally open position for breathing through the vent if the controller is not powered and/or operating the flow generator. When under power and operating, the controller may then control the vent to limit vent flow to any desired $CO_2$ washout level.

Patient Comfort Vent Control

Patient compliance with OSA therapy such as CPAP and APAP is affected by many factors. One of the significant factors affecting success of an OSA patient remaining on effective therapy is the level of comfort associated with the wearing of the device and mask during the period while still awake. If the patient comfort can be paramount until the onset of sleep then there is likely to be an increased compliance with CPAP or APAP therapy overall. Similarly, the patient may resist continuation of therapy if woken for any reason during sleep. The awakening may be unrelated to the patient condition, for example the arrival home of another family member may wake the patient. Once awake, the patient may suffer discomfort and remove the CPAP system.

One factor that may decrease patient comfort, especially when not sleeping or in an aroused state, is the potentially low pressure during wake state of an APAP machine. Typically an APAP machine uses low pressure when the wearer is not experiencing an occluded airway. For fixed aperture vented mask systems the low pressure also will result in a low intentional leak (or vent) flow and may result in decreased $CO_2$ washout. Potentially, the patient may experience some re-breathing, while not significantly of clinical concern it may be sufficiently uncomfortable to the patient and discourage use of the mask system.

Potentially, due to the low washout levels and additionally the level of humidity and heating levels of the air proximal to the patient airways in the conduit and mask, the patient may feel uncomfortable.

During treatment and the period waiting to fall asleep and also during potential arousal events, the patient may suffer a feeling similar to claustrophobia where there is a desire to remove the CPAP/APAP system.

A variable vent system, such as one that employs the conduits and vents previously described, can potentially improve comfort during sleep state periods, including wake, when therapy is not required. For example, a controller of the adjustable vent may detect appropriate sleep related periods of a patient, such as wake, or potentially light sleep. In response to these detections, the controller may then alter the pneumatic, humidity and heat settings set by the controller.

For example, the controller may increase the vent flow when the respiratory treatment apparatus is set to generate lower pressures. Similarly, the controller may decrease the vent flow when the respiratory treatment apparatus is set to generate higher pressures. This may be suitable if these pressure settings contribute to events that may wake or result in patient arousal.

When increasing the vent flow at lower pressures, the APAP/CPAP respiratory treatment device could compensate by increasing the flow supply from the controlled flow generator to maintain the set pressure at the patient interface but with increased flow through the conduit and mask and out the vent. The result is significantly increased $CO_2$ washout at the desired pressure setting.

This controlled adjustment may also result in a change in feeling of the patient as the flows near the facial skin and nasal nares may have a cooling and drying effect. Similarly, reducing the vent flow may increase the feeling of the temperature and moisture content of the air to the patient.

By changing the vent flow, the patient may feel hotter/cooler, moist or dry changing simply with the flow rate of the air near sensitive skin and nasal tissue. Thus, the regulation of vent flow can provide a basis for adjusting patient comfort.

In some embodiments, the detection of sleep state may serve as a basis to change the vent flow to improve the patient's feeling of comfort. Similarly, the humidity and delivered air temperature may also be optimised to suit the patient during such conditions in the event that the controller of the respiratory treatment apparatus also controls a humidifier and/or air warming element.

If normal or deeper sleep states are detected by the controller, the prescribed patient therapy (e.g., CPAP and APAP therapy settings), humidity and temperature settings will be set and delivered by the apparatus.

However, comfort changes from the prescribed treatment settings may be set when the apparatus detects light sleep or awake states. The physician prescribed settings during these states may not be necessary since OSA is not likely to occur during such stages of sleep (or awake) states. Thus, patient preferred settings may automatically take effect on the detection of the light sleep or awake states.

Such features as a "ramp" and similar from current CPAP machines do not deliver the prescribed titration level of pressure until the patient is expected to be in the correct sleep state by delaying the delivery of therapeutic pressure levels for a period of time by gradually raising the pressure to the therapeutic level.

A further feature can exploit the lack of need for therapeutic pressures during light sleep or awake states to allow the patient to adjust the flow through the vent during such states. Normal therapeutic settings can resume during usual sleep states requiring it. For example, when the "ramp" feature is engaged, the respiratory treatment apparatus may set the vent flow levels to those specified by some "patient comfort" settings rather than the prescribed therapeutic settings. Thus, the apparatus may have a user interface to allow the patient to input or adjust the "patient comfort" settings (e.g., within permitted ranges) to the apparatus for these controlled features.

As an extension and as part of the "patient comfort" settings, the apparatus may permit the patient to adjust CPAP/APAP pressure within the safe limits that may be set by clinical staff during titration or to some range that may be found to be safe during the detected awake or light sleep periods.

Similarly, as part of the "patient comfort" settings, the patient may be able to have favored humidity and heat settings during such sleep phases that revert to needs based settings in other sleep states.

In some cases, the settings may be automatically controlled or adjusted by the respiratory treatment apparatus based on detected environmental conditions such at temperature and/or humidity outside of the device. For example, cooler settings may be utilized during warmer seasons and warmer settings may be utilized during cooler seasons.

There may be a plethora of settings and/or "patient comfort" profiles of settings that may be preferred by the patient, or even the clinical or prescribing staff. The different profiles even for a single patient may be activated by the device depending on various detected conditions, such as a particular sleep state, environmental conditions, etc.

For example, the apparatus may be configured to activate a particular preferred profile of the air delivery parameters that improve patient comfort at a preferred automatic time or particular sleep state.

Priority in control or profile may be given to comfort, pressure, flow ($CO_2$ washout), moisture, heat, battery or power supply endurance, noise, machine/consumable part life or other system parameter that may be preferred.

In a particular example, an OSA respiratory treatment apparatus may be configured to deliver pressure, vent flow ($CO_2$ washout), humidity/moisture and/or heat to the tastes of the patient as set in "patient comfort" settings by a user interface of the apparatus. Any combination of parameters pressure, flow, moisture and temperature of delivered air may be profiled individually or in any combination. The patient comfort settings then may be activated depending on the particular detected conditions of the machine such as sleep state (e.g., awake or light sleep) and/or environmental conditions. When prescribed therapy is required, such as during detected sleep states, physician prescribed "therapeutic settings" may then be activated such that some or all of the comfort settings will be deactivated.

Therapeutic Vent Control

Figure 14:
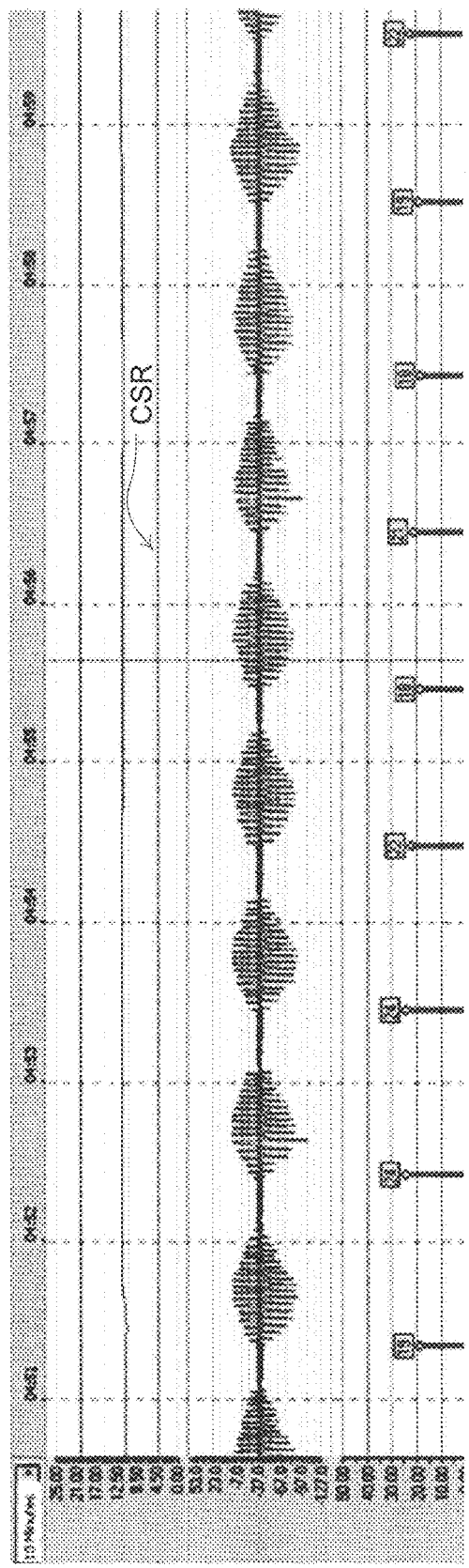
FIG. 14 is an illustration of a Cheyne-Stokes breathing pattern.

Cheyne-Stokes respiration (CSR), Complex Sleep Apnoea and other forms of central sleep apnoea may be characterised as (on-average) hyperventilation during sleep. This hyperventilation frequently manifests itself as a lower-than-normal daytime $PaCO_2$. However, it is mainly CHF—or altitude-related periodic breathing with that association—that can be predicted from daytime $PaCO_2$. Complex Sleep Apnoea cannot typically be predicted from daytime $PaCO_2$. The graph of FIG. 14 shows the typical waxing and waning pattern of CSR in a patient getting CPAP treatment from a CPAP respiratory treatment apparatus. The pattern is characterized by periods of hyperventilation (hyperpnoea) interspersed with periods of low ventilation (hypopnoea) or central apnoea. The pattern is strikingly periodic with little variation neither in the length of each cycle nor in the length of the components of each cycle.

Therapeutic methods to return $PaCO_2$ to a normal range have focussed on restoring a normal breathing pattern. For example, the ResMed AutoSet CS (or VPAP Adapt) is a non-invasive pressure-control ventilator that stabilises $PaCO_2$ by increasing pressure support during periods of apnoea or hypopnoea and decreasing pressure support during periods of above-normal or normal ventilation. This method acts to 'break' the vicious cycle whereby hyperventilation drives the patient's $PaCO_2$ below the apnoeic threshold which in-turn leads to a new cycle of hyperventilation. By servo-ventilating short term ventilation to a target which is a fraction of a longer term ventilation, the CSR pattern is often abolished. The ventilator has sensors and methods to reliably measure patient respiratory flow in the presence of a known mask vent flow and a variable inadvertent mask leak. The ventilation measures are derived from the patient respiratory flow estimate.

Another way to abolish or ameliorate the CSR pattern is by having the patient re-breathe some fraction of their own exhaled $CO_2$. The rebreathed $CO_2$ acts to either raise the patient's $PaCO_2$ or to prevent $PaCO_2$ from falling during hyperventilatory phases. In this way it can reduce the drive to hyperventilate. A convenient way to do this is to have an actively controlled vent at the mask such as one of the embodiments previously described. In existing vented breathing systems, the vent is a fixed orifice which provides enough flow over the expected mask pressure range to adequately purge the mask of exhaled $CO_2$ over each breathing cycle. By controlling the vent orifice, the amount of $CO_2$ rebreathed by the patient can also be controlled. Such an actively controlled vent can form part of a servo-control system of a respiratory treatment apparatus.

In one example, the respiratory treatment apparatus, such as a ventilator, may implement a fixed hyperventilation threshold setting, such as in liters per minute (LPM). This setting may be set by a clinician before the start of therapy. If the patient's average measured ventilation (measured over a period such as three minutes) were to exceed the threshold, the vent may be actively controlled by the controller to reduce the flow such as by reducing its venting size such that the patient would start to re-breath a small fraction of their own $CO_2$. If the detected hyperventilation subsequently resolved, such as if the threshold is no longer exceeded, the vent could be controlled by the controller to return to a normal position.

In another alternative approach, a servo-control mechanism of the controller may continuously adjust the vent size to keep fresh gas ventilation under a pre-determined threshold. Such a servo-controlled system might utilise a PID type controller with the error signal being the degree to which ventilation was above threshold and it would output the size of the vent. The controller could also regulate the vent size so as to constrain it to be within pre-determined maximum and minimum sizes.

In another example, instead of a fixed ventilation threshold, there might be an index of ventilation instability. For example, the following indices may serve as a single measure or combined measure of ventilation instability:

a. Ventilation stability may be measured by a moving window standard-deviation of ventilation assessed by the controller;

b. A central apnoea index, a central hypopnoea index or a central apnoea-hypopnoea index as detected by the controller;

c. An apnoea-hypopnoea index (which persists despite automatic adjustment of EPAP to abolish upper airway obstruction) as detected by the controller;

d. A respiratory disturbance index, (e.g., an arousal index such as one derived from flow, $SpO_2$ and/or photoplethysmogram) as detected by the controller.

Methods for detection and automated determination of such indices may be considered in view of the discussion of PCT/AU2010/000894, filed Jul. 14, 2010, based on U.S. Provisional Patent Application No. 61/226,069 filed Jul. 16, 2009, the disclosures of which are incorporated herein by reference.

In each case, the vent orifice size may be adjusted either in step fashion or continuously so as to minimise the measure of ventilation instability. Optionally, the controlled changes to vent size could be between two size chosen for 'normal' breathing and "re-breathing" or it may be continuously adjustable through many sizes in a range between fixed preset limits.

FIGS. 15A and 15B show a simulated CSR flow pattern and some filter outputs plotted on a common time scale. The trace in FIG. 15A is a simulated patient flow with CSR breathing bracketed by two periods of normal breathing. The plot of FIG. 15B shows a ventilation measure VM (filtered with a three minute time constant) and the moving window standard deviation SD of the ventilation measure taken from the simulated patient flow of FIG. 15A. Allowing for the time it takes the filters to initialize (slow rise at the beginning), it can be seen that the ventilation during the CSR period is a) higher on-average and b) variable. The standard deviation SD trace shows that the instability in the ventilation can be measured by a moving window SD metric.

As previously mentioned, in some embodiments, the adjustable vent may be controlled by an actuator and servo-controlled to minimise a respiratory disturbance index. For example, in the plot of FIG. 15B, the determined rise in the widowed standard deviation SD of ventilation would cause the controller to reduce the vent size to increase the fraction of inspired $CO_2$. Then, when the windowed SD reduced, the controller would begin reopening or increasing the area of the vent.

In another example, the controller of the respiratory treatment apparatus may 'phase lock' to the CSR cycle. This process would involve learning the CSR cycle via a phase-locked loop and then adjusting the vent area so as to initiate a rebreathing cycle for the optimum time and with the optimum phase relationship to the CSR cycle. This would result in a lower on-average amount of rebreathing compared to a fixed level or a quasi-statically adjusted level.

In such a case, the CSR cycle is typically 60 seconds in length with a typical range of between 40 and 90 seconds. In general, the cycle length increases with worsening heart failure HF (e.g., bad O reference) as does the hyperpnoea length. The cycle length does not vary quickly or substantially within a night. Therefore, once a system had phased locked to a CSR cycle, it may be possible to maintain phase lock despite a lessening degree of CSR amplitude modulation. Alternatively, if the CSR signal were to disappear altogether (i.e., normal breathing resumed) then the apparatus may re-establish a phase lock quickly based on a previously learned cycle length, hyperpnoea length and apnoea or hypopnoea length, or metrics indicative of these features.

If the patient is experiencing a CSR pattern with frank apnoeas, it may only be possible to initiate rebreathing during the hyperpnoea phase (i.e., while the patient is actually spontaneously breathing). However, once apnoeas have been abolished by the apparatus and a CSR pattern with continuous spontaneous breathing throughout the breathing cycle is detected, then it may be advantageous to vary the controlled rebreathing process to the optimum point in the cycle and for the optimal length that minimises the instability to the greatest extent. This phase delay and length of the rebreathing cycle might be pre-programmed or learned after starting at a predetermined 'best guess' starting point.

In some cases, the apparatus may simply monitor the patient over time by recording the CSR metrics previously mentioned. The apparatus may then evaluate the metrics and recommend use of a vent having a lesser venting flow if residual CSR exists. For example, the apparatus may reference an array of standard vents to choose from with particular vent flow characteristics, the apparatus may determine that a step down to a smaller vent should be implemented by issuing a warning or text instruction. Optionally, in the case of constant flow venting, it may suggest an adjustment to the vent such as a manual adjustment or insertion of an alternate mylar tab or vent aperture that will make some change to the flow characteristics of the vent.

In the above examples, the active vent control system can be run at each treatment session (e.g., each night) to provide therapy to the patient in a real time detection/response to patient needs. However, in some embodiments, it might be used on one or more nights to determine a suitable fixed vent size for the patient's subsequent therapy (e.g., by implementing a vent flow titration protocol.)

In the examples above, the active vent system and associated control system for rebreathing could be used in conjunction with adaptive servo-ventilation (e.g., ResMed AutoSet CS2). In such a combined system, the pressure control adjustment process might be used as the primary driver for suppression of CSR breathing and a rebreathing control process as previously described might supplement that process, in tandem, to damp out any residual instability (if it is detected). Alternatively, the two systems might work in concert with a master process controlling both pressure-support and rebreathing via active vent in order to more simultaneously operate to stabilise ventilation to the greatest degree. For example, such a system might implement a pressure support control-loop acting with a 'fast' time constant and a rebreathing control process acting with a 'slow' time constant.

In another example, the rebreathing control process might be the primary means of suppressing CSR breathing, with the ventilator pressure support component acting to suppress frank apnoeas via the insertion of backup breaths.

In some embodiments, phasic venting may be implemented with a venting protocol to treat CSR. For example, during detected hyperpnoea periods, the controller may adjust the vent to close or reduce the venting area to treat the hyperpnoea but only during detected patient expiration. In such a case, the vent area would be increased during inspiration.

In another embodiment, a process of the controller may directly regulate rebreathing by calculating or estimating the quantity of flow out through the vent and controlling it to be at a desired quantity or percent.

In embodiments with the aforementioned technology, a pressure treatment therapy is generated by a respiratory treatment apparatus that also includes the venting control. However, in some embodiments a mask with a vented control may be used without a flow generator that generates a pressure treatment (e.g., a snorkel) or in some cases pressure treatment may be stopped while venting control is activated.

Example Controller Architecture

Figure 16:
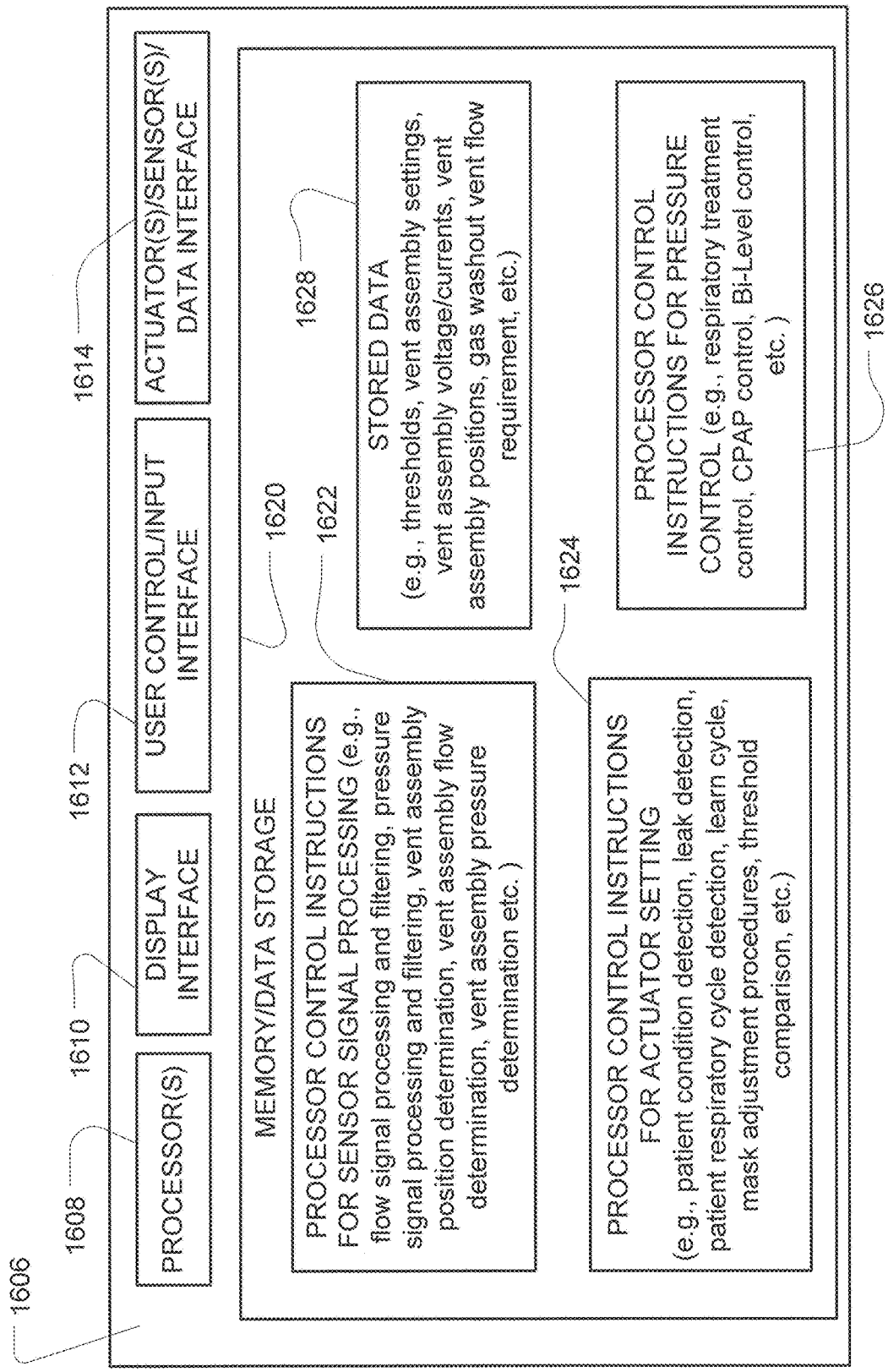
FIG. 16 is a schematic illustrating an example architecture of a controller for controlling adjustment of the variable vents of the present technology.

An example system architecture of a controller of a respiratory treatment apparatus suitable for controlling actuation of the variable area vent assembly of the present technology is illustrated in the block diagram of FIG. 16. In the illustration, the controller 1606 for a respiratory treatment apparatus may include one or more processors 1608. The system may also include a display interface 1610 to output event detection reports (e.g., central apnea, obstructive apnea, central hypopnea, obstructive hypopnea, etc.) or vent assembly related data (settings, vent flow vs. time plots, vent area, etc.) as described herein such as on a monitor or LCD panel. This may be used to log and/or monitor the performance or controlled changes in the vent characteristics during a treatment session. A user control/input interface 1612, for example, a keyboard, touch panel, control buttons, mouse etc. may also be provided to activate or modify the control methodologies described herein. The system may also include an actuator, sensor or data interface 1614, such as a bus, for receiving/transmitting data such as programming instructions, pressure and flow signals, positioning signals, actuator control signals, etc. The device may also typically include memory/data storage components 1620 containing control instructions of the aforementioned methodologies. These may include processor control instructions for sensor signal processing (e.g., flow and/or pressure signal processing and filtering, vent assembly position determination, vent assembly flow determination, vent assembly pressure determination, etc.) at 1622. These may also include processor control instructions for control of the variable vent area vent assembly actuation/setting (e.g., patient condition detection, leak detection, patient respiratory cycle detection, learn cycle, sleep detection, mask adjustment procedures, related threshold comparisons, etc.) at 1624 as previously discussed in more detail herein. These may also include processor control instructions for treatment control (e.g., respiratory treatment control, pressure adjustments, CPAP pressure control, Bi-level pressure control, or other flow generator control methodologies etc.) at 1626. Finally, they may also include stored data 1628 for or from the methodologies of the controller (e.g., vent assembly settings, vent assembly voltage and/or current data, vent assembly positions, gas washout flow requirements data, recorded vent flow data, etc.).

In some embodiments, these processor control instructions and data for controlling the above described methodologies may be contained in a computer readable recording medium as software for use by a general purpose computer so that the general purpose computer may serve as a specific purpose computer according to any of the methodologies discussed herein upon loading the software into the general purpose computer. Still further, the methodologies may be contained in a device or apparatus that includes integrated chips, a memory and/or other control instruction, data or information storage medium. For example, programmed instructions encompassing such detection methodologies may be coded on integrated chips in the memory of the device or apparatus to form an application specific integrated chip (ASIC). Such instructions may also or alternatively be loaded as software or firmware using an appropriate data storage medium.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

While particular embodiments of this technology have been described, it will be evident to those skilled in the art that the present technology may be embodied in other specific forms without departing from the essential characteristics thereof. The present embodiments and examples are therefore to be considered in all respects as illustrative and not restrictive, the scope of the technology being indicated by the appended claims rather than the foregoing description, and all changes which come within the meaning and range of equivalency of the claims are therefore intended to be embraced therein. It will further be understood that any reference herein to subject matter known in the field does not, unless the contrary indication appears, constitute an admission that such subject matter is commonly known by those skilled in the art to which the present technology relates.

The invention claimed is:

1. An apparatus for automated control of gas washout of a patient interface of a respiratory treatment apparatus comprising:

a vent assembly having a variable exhaust area, the vent assembly being associated with a patient interface to vent expiratory gas, the vent assembly including a spherical diverter and a conduit casing that houses the spherical diverter, the spherical diverter having a flow bore configured to deliver the expiratory gas to one or more vent openings of the conduit casing for venting; and an actuator to manipulate orientation of the spherical diverter to vary size of the exhaust area of the conduit casing.

2. The apparatus of claim 1 wherein rotation of the spherical diverter positions the flow bore to selectively permit a transfer of gas through the flow bore within the conduit casing of the vent assembly.

3. The apparatus of claim 2 wherein rotation of the spherical diverter selectively positions a surface of the spherical diverter to selectively block a transfer of gas through one or more exhaust ports of the conduit casing of the vent assembly.

4. The apparatus of claim 3 wherein the conduit casing further comprises a muffler chamber proximate to one or more exhaust ports of the conduit casing.

5. The apparatus of claim 1 further comprising a controller including a processor, the controller coupled with the actuator, the controller configured to operate the actuator to adjust the size of the exhaust area of the vent assembly.

6. The apparatus of claim 1 wherein the actuator comprises a motor, a shaft of the motor coupled with the spherical diverter.

7. The apparatus of claim 6 further comprising a position sensor, the position sensor configured to detect a rotational position of the spherical diverter.

8. The apparatus of claim 1 wherein the spherical diverter comprises a spherical surface configured to selectively block a transfer of gas through an exhaust port.

9. The apparatus of claim 1 wherein rotation of the spherical diverter selectively positions the flow bore to divert a transfer of gas from the conduit casing through a plurality of exhaust ports on opposing sides of the conduit casing.

10. The apparatus of claim 1 wherein rotation of the spherical diverter selectively positions both a first and a second surface of the spherical diverter such that the first surface closes a path of the conduit casing to a transfer of gas through the conduit casing and the second surface centrally and partially blocks a transfer of gas through the conduit casing while permitting a transfer of gas around the second surface and through a plurality of exhaust ports on opposing sides of the conduit casing.

11. The apparatus of claim 1 wherein the spherical diverter has a plurality of separate flow bores.

12. The apparatus of claim 11 wherein one of the plurality of separate flow bores is a concave recess in the spherical diverter that forms a J-channel.

* * * * *